United States Patent [19]

Chao

[11] Patent Number: 6,052,433
[45] Date of Patent: *Apr. 18, 2000

[54] APPARATUS AND METHOD FOR DUAL-ENERGY X-RAY IMAGING

[75] Inventor: Yong-Sheng Chao, Storrs, Conn.

[73] Assignee: Advanced Optical Technologies, Inc., E. Hartford, Conn.

[*] Notice: This patent is subject to a terminal disclaimer.

[21] Appl. No.: 09/025,926

[22] Filed: Feb. 19, 1998

Related U.S. Application Data

[63] Continuation-in-part of application No. 08/725,375, Oct. 3, 1996, Pat. No. 5,771,269, which is a continuation-in-part of application No. 08/580,602, Dec. 29, 1995, Pat. No. 5,648,997.

[51] Int. Cl.[7] ........................................................ H05G 1/64
[52] U.S. Cl. ......................... 378/98.9; 378/98.12; 378/147
[58] Field of Search ............................... 378/4, 19, 5, 62, 378/98.4, 98.2, 98.11, 98.12, 98.9, 147, 149, 154, 901

[56] References Cited

U.S. PATENT DOCUMENTS

| 4,389,729 | 6/1983 | Stein . | |
|---|---|---|---|
| 4,792,900 | 12/1988 | Sones et al. . | |
| 4,829,552 | 5/1989 | Rossi et al. . | |
| 5,148,455 | 9/1992 | Stein . | |
| 5,440,647 | 8/1995 | Floyd, Jr. et al. . | |
| 5,648,997 | 7/1997 | Chao | 378/98.4 |
| 5,771,269 | 6/1998 | Chao | 378/5 |

FOREIGN PATENT DOCUMENTS

| 0 105 618 | 4/1984 | European Pat. Off. . |
| 0 218 923 | 4/1987 | European Pat. Off. . |

OTHER PUBLICATIONS

Lehmann et al., Generalized Image Combinations in Dual KVP Digital Radiography, 8 Medical Physics 659 (Sep./Oct. 1981).

Chan et al., Studies of Performance of Antiscatter Grids in Digital Radiography: Effect on Signal–to–Noise Ratio, 17 Medical Physics 655 (Jul./Aug. 1990).
Chuang et al., Comparison of Four Dual Energy Image Decomposition Methods, 4 Physics in Medicine and Biology 455 (1988).
Seibert et al., X–Ray Scatter Removal by Deconvolution, 15 Medical Physics 567 (Jul./Aug. 1988).
Stewart et al., Single Exposure Dual–Energy Computed Radiography, 17 Medical Physics 866 (Sep./Oct. 1990).
Honda et al., A Technique of Scatter–Glare Correction Using a Digital Filtration, 20 Medical Physics 59 (Jan./Feb. 1993).
Cardinal et al., An Accurate Method for Direct Dual–Energy Calibration and Decomposition, 17 Medical 327 (May/Jun. 1990).
Wahner et al., The Evaluation of Osteoporosis: Dual Energy X–Ray Absorptiometry in Clinical Practice 14–33 (1994).
Yaffe et al., Scatter Radiation in Diagnostic Radiology: Magnitudes, Effects, and Methods of Reduction, 8188 Journal of Applied Photographic Engineering vol. 9 (1983).
Wagner et al., Dual–Energy X–Ray Projection Imaging: Two Sampling Schemes for the Correction of Scattered Radiation, 15 Medical Physics 732 (Sep./Oct. 1988).

(List continued on next page.)

Primary Examiner—David P. Porta
Attorney, Agent, or Firm—Morse & Altman

[57] ABSTRACT

Apparatus and method for performing dual-energy x-ray imaging using two-dimensional detectors. The apparatus consists of, in physical order, an x-ray source, a front two-dimensional x-ray detector, a beam selector, and a rear two-dimensional x-ray detector. The subject is located between the x-ray source and front detector. The beam selector prevents primary x-rays from reaching selected locations of the rear detector. A pair of primary dual-energy images is obtained at the rear detector. Using a dual-energy data decomposition method, a low-resolution primary x-ray front detector image is calculated, from which a high-resolution primary dual-energy image pair is calculated. In addition, the data decomposition method can be used to calculate a pair of high-spatial-resolution material composition images.

29 Claims, 9 Drawing Sheets

OTHER PUBLICATIONS

Lo et al., Scatter Compensation in Digital Chest Radiography Using the Posterior Beam Stop Technique, 21 Medical Physics 435 (Mar. 1994).

Boone et al., Monte Carlo Simulation of the Scattered Radiation Distribution in Diagnostic Raiology, 15 medical Physics 713 (Sep./Oct. 1988).

Archer et al., Laplace Transform Pair Model for Spectral Reconstruction, 9 Medical Physics 844 (Nov./Dec. 1982).

Lee et al., A New Digital Detector for Projection Radiography, SPIE (Feb. 1995).

Petrone et al., Rare–Earth Scatter Fractions in Chestt Radiography, 20 Medical Physics 475 (Mar./Apr. 1993).

Zhao et al., Digital Radiology Using Self–scanned Readout of Amorphous Selenium, 1896 SPIE Physics of Medical Imaging 114 (1993).

Antonuk et al., Demonstration of Megavoltage and Diagnotic X–ray Imaging with Hydrogenated Amorphous Silicon Arrays, 19 Medical Physics 1455 (Nov./Dec. 1992).

Floyd et al., Quantatative Scatter Measurement in Digital Radiogrphy Using Photostimulable Phosphor Imaging System, 18 Medical Physics 408 (May/Jun. 1991).

Zhao et al., A Large Area Solid–State Detector for Raiology Using Amorphous Selenium, 1651 SPIE Medical Imaging IV: Instrumentation 134 (1992).

Honda et al., Method for Estimating the Intensity of Scattered Radiation Using a Scatter Generation Model, 18 Medical Physics 219 (Mar./Apr. 1991).

Archer et al. Laplace Reconstruction of Experimental Diagnostic X–ray Spectra, 15 Medical Physics 732 (Nov./Dec. 1988).

Boone et al., An Analytical Model of the Scattered Radiation Distribution in Diagnostic Radiology, 15 Medical Physics 721 (Sep./Oct. 1988).

Vetter et al., Correction for Scattered Radiation and Other Background Signals in Dual–Energy Computed Tomography Material Thickness Measurements, 15 Medical Physics 726 (Sep./Oct. 1988).

Speller et al., Monte Carlo Study of Multiple Scatter Effects in Compton Scatter Sitometry, 15 medical Physics 707 (Sep./Oct. 1988).

APPARATUS AND METHOD FOR DUAL-ENERGY X-RAY IMAGING

RELATED APPLICATIONS

The present application is a continuation-in-part of U.S. patent application Ser. No. 08/725,375, dated Oct. 3, 1996 now U.S. Pat. No. 5,771,269, which is a continuation-in-part of U.S. patent application Ser. No. 08/580,602, filed Dec. 29, 1995 now U.S. Pat. No. 5,648,997, issued Jul. 15, 1997, for APPARATUS AND METHOD FOR REMOVING SCATTER FROM AN X-RAY IMAGE in the name of Yong-Sheng Chao.

GOVERNMENT FUNDING

The research involved in this application was funded in part by the National Aeronautics and Space Administration, contract number NAS 9-19061. The intellectual property rights of the applicant and the government of the United States of America are governed by 37 CFR 401.

BACKGROUND OF THE INVENTION

1. Field of the Invention

The present invention relates generally to digital x-ray imaging and, more particularly, relates to methods and apparatuses for two-dimensional dual-energy x-ray imaging.

2. The Prior Art

Recent advances in the field of semiconductor fabrication have resulted in the ability to fabricate large-format two-dimensional integrated detector arrays for x-ray detection. These detector arrays have on the order of millions of detector cells and provide instant acquisition of two-dimensional x-ray images with exceedingly high quality. The capability of these detector arrays will not be confined to providing only qualitative visual images, but also have great potential for quantitative imaging.

Dual-energy x-ray imaging is an accurate quantitative technique that can decompose a pair of subject images acquired at two energy levels into two images, each representing one material composition image of the subject. Current dual-energy x-ray imaging techniques are limited to using linear detector arrays. If dual-energy x-ray imaging can be further improved to use recently developed large format detector arrays, the capabilities of clinical x-ray diagnosis can be significantly enhanced. For example, dual-energy x-ray imaging could be used for improved diagnosis of breast cancer in mammography, for quantitatively predicting elderly bone fractures in bone imaging, and for improved diagnosis of pulmonary diseases in chest imaging.

There are two significant technological barriers for combining dual-energy methods and large format detector arrays together. First, the prior art dual-energy x-ray data decomposition methods are not suitable for use with large format two-dimensional detectors. The underlying reason is that current methods either require the user to make frequent judgments on a pixel-by-pixel basis in the process of data decomposition, or to use a mechanical device to exchange data interactively with the computer on a pixel-by-pixel basis. Such approaches are not suitable for analyzing data volume with millions of pixels per image frame. Second, large-format detector arrays are susceptible to substantial scatter distortions, whereas dual-energy x-ray imaging requires that primary image data be used.

SUMMARY OF THE INVENTION

The present invention comprises apparatus and methods for performing dual-energy x-ray imaging by using large format two-dimensional detectors. There are two major goals for performing dual-energy x-ray imaging. The first is to use the dual-energy imaging method to remove the scatter. The second goal is to determine two material composition images of the image subject. There are several hardware components of the apparatus in physical sequence from front to back. (1) An x-ray source emits x-rays. (2) A front two-dimensional detector array receives primary x-rays and scatter x-rays. (3) A beam selection means blocks the passage of primary x-rays along a number of travel directions, while allowing passage of primary x-rays along other directions. Scatter x-rays are passed generally unaffected. (4) A rear two-dimensional detector assembly receives the scatter x-rays and primary x-rays passed through the beam selection means. Because of the operation of the beam selection means, the rear detector assembly receives only scatter x-rays at a number of detection locations, while at other detection locations, the rear detector assembly receives both primary and scatter x-rays.

The most important component of the method for performing dual-energy x-ray imaging in the present invention is a data decomposition method based on directly solving a dual-energy x-ray imaging equation system without relying on linearization approximations. This method establishes a direct two-way relationship between the dual-energy primary x-ray image pair and the material composition image pair. Based on the dual-energy data decomposition method, when a pair of dual-energy primary images is given, the two material composition images can be automatically computed without user intervention. The reverse is also true. Another component of the method is the exact procedures for performing dual-energy x-ray imaging based on use of the hardware system and the data decomposition method.

First, a summary of the dual-energy x-ray data decomposition method of the present invention is in order. The method directly solves the nonlinear dual-energy x-ray imaging fundamental equation system in its original form without relying on any linear or second order approximations. The method includes: (1) Constructing an explicit quantitative equation system $D_H=F_{DH}(b,s)$ and $D_L=F_{DL}(b,s)$ for each detector according to the nonlinear dual-energy x-ray imaging fundamental equation system in its original form and saving them for later use, where $D_H$ represents the low-energy primary x-ray signal and $D_L$ represents the high-energy primary x-rays signal. The two equations and all quantities therein are for a typical single detector cell; the entire detector array can be represented by a single detector cell after normalization. (2) Reconstructing a three-dimensional surface equation system $b=b(D_H, D_L)$ and $s\times s$ $(D_H, D_L)$ by numerically inverting the equation system of step 1 and saving them for later use. (3) Determining the desired values for b and s at each individual detector cell location by inserting the available data pair $(D_H, D_L)$ into the numerical equations of step 2 or, conversely, when a pair of b and s values are given, determining the desired values for $D_H$ and $D_L$ at each individual detector cell location by inserting the available data pair (b,s) into the numerical equations of step 1. (4) Maintaining the accuracy at each step to be as high as real number analytical solutions can provide.

The most important procedures for performing dual-energy x-ray imaging include the following steps: (1) Acquire a pair of image data for the rear detector assembly at a higher energy level H and a lower energy level L of x-rays. Because of the function of the beam selection means, in the acquired image data, a number of detector cells contain only scatter x-ray signals, while the other detector cells contain a combination of primary x-ray signals and scatter x-ray signals. (2) Derive a pair of dual-energy primary image data for the rear detector assembly from the directly received data of step 1. The necessity for obtaining primary x-ray image data is that only primary x-ray image data can be used for dual-energy x-ray imaging. How the derivation is performed is explained below. (3) Use dual-energy data decomposition method to calculate a low-resolution primary image for the front detector from the dual-energy primary image pair of the rear detector. This is one of the most important aspects of the present invention. (4) Acquire a high-resolution image for the front detector either at the higher energy level H or at the lower energy level L according to the practical need. Because the low-resolution primary x-ray image on the front detector has been calculated using the acquired high-resolution image data together with the calculated low-resolution primary image data, the scatter image, as well as the primary image with high spatial resolution, can be calculated for the front detector. Upon completion of step 4, one of the major goals for performing dual-energy x-ray imaging has been accomplished: to improve the image quality of the front detector by removing the undesired scatter from the front detector signals. (5) To proceed, a pair of primary x-ray images of the front detector can be acquired at two energy levels L and H instead of only one image as in step 4. By further using the dual-energy data decomposition method, the two material composition images for the image subject at a high spatial resolution can be obtained. Thus, step 5 fulfills the second goal of dual-energy x-ray imaging.

The present application differs from related patent application Ser. No. 08/725,375 and related issued U.S. Pat. No. 5,648,997 in the structure of the beam selection means. In these related publications, the beam selection means blocks scatter x-rays to selected locations of the rear detector. In the present invention, the beam selection means blocks primary x-rays to particular locations of the rear detector. Because different signals are allowed to reach the rear detector, a different method for deriving the low-resolution primary x-ray image is used. In the related publications, the low-resolution primary x-ray image is acquired directly from the rear detector. In the present invention, the low-resolution primary x-ray image must be calculated from a low-resolution primary x-ray image and a low-resolution scatter/primary composite x-ray image acquired from the rear detector.

The object of the present invention is to provide an apparatus and a method for dual-energy x-ray imaging using large format two-dimensional detectors. The results of dual-energy x-ray imaging can provide two material composition images of a subject with a spatial resolution as high as the two-dimensional detector array can provide. Meanwhile, dual-energy x-ray imaging can significantly improve the quality of the front detector by removing the undesired scatter distortion.

Another object is to provide a dual-energy data decomposition method based on directly solving a nonlinear dual-energy fundamental equation system without relying on current linearization approximations. As a result, the dual-energy image data decomposition can be automatically carried out by computer without user intervention.

BRIEF DESCRIPTION OF THE DRAWINGS

For a fuller understanding of the nature and object of the present invention, reference is made to the accompanying drawings, wherein:

FIG. 2a presents an energy spectrum at a high voltage HV=70 kV and FIG. 2b presents an energy spectrum at a high voltage HV=150 kV;

DETAILED DESCRIPTION

Introduction

The present invention comprises apparatus and methods for performing dual-energy x-ray imaging using two-dimensional detectors. Two preferred embodiments are described. First the apparatus is described. Then, after explaining the mathematical and physical foundations, the procedures for dual-energy imaging are outlined.

First Embodiment

As shown in FIG. 1, the subject under examination 12 is located between the x-ray source 14 and the front detector 16. The x-ray source 14 emits two consecutive pulses, a high-energy pulse at an average energy level H followed by a low-energy pulse at an average energy level L. In an alternate configuration, the low-energy pulse is emitted first. Preferably, in both configurations, the high-energy pulse has an average x-ray energy from approximately 25 keV to approximately 250 keV and the low-energy pulse has an average x-ray energy from approximately 15 keV to approximately 60 keV, with the high-energy pulse always higher in energy than the low-energy pulse.

Figure 2A:
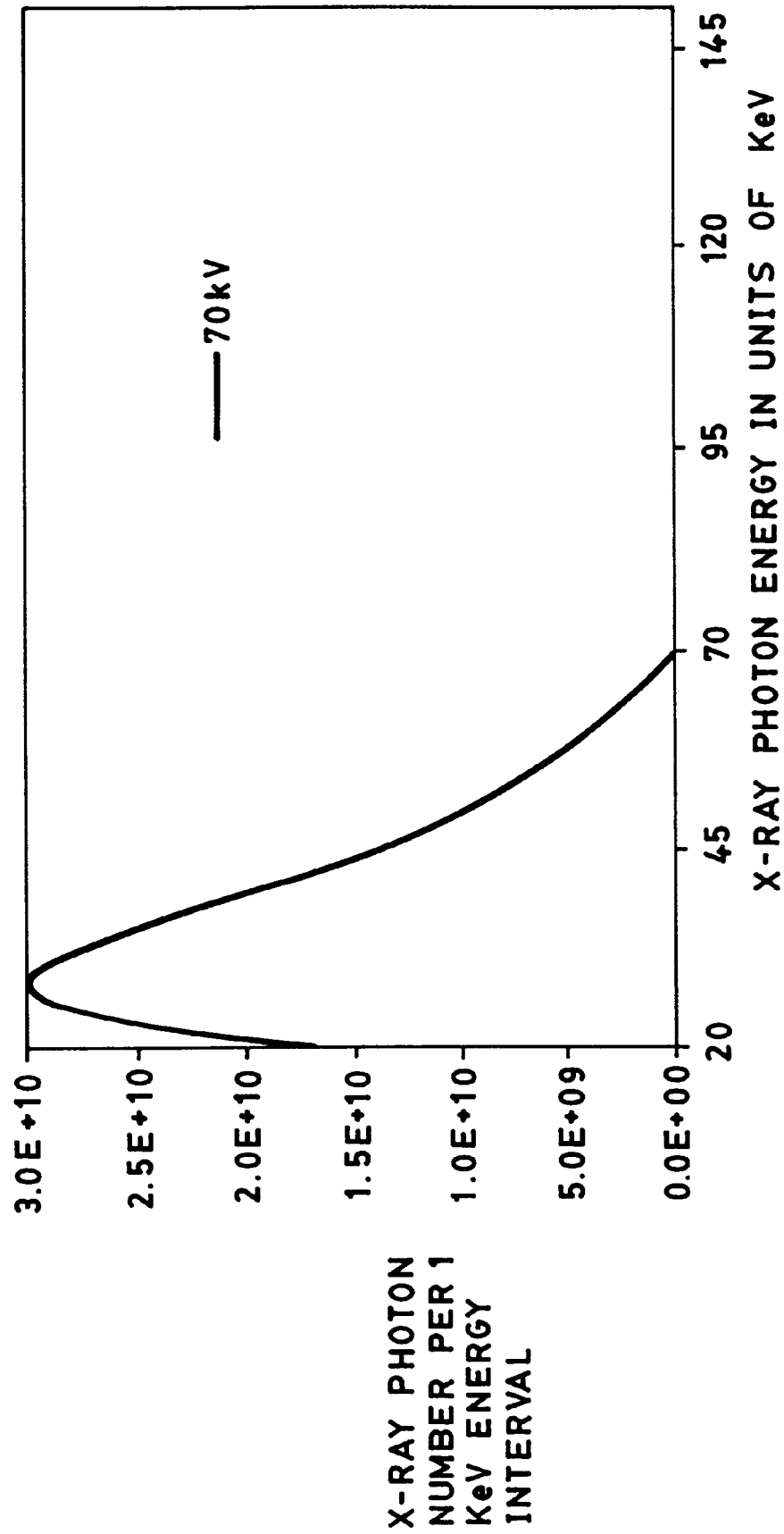
FIGS. 2a and 2b are curves describing typical x-ray source energy spectra at the higher energy level H and lower energy level L used in the present invention, where
Figure 2B:
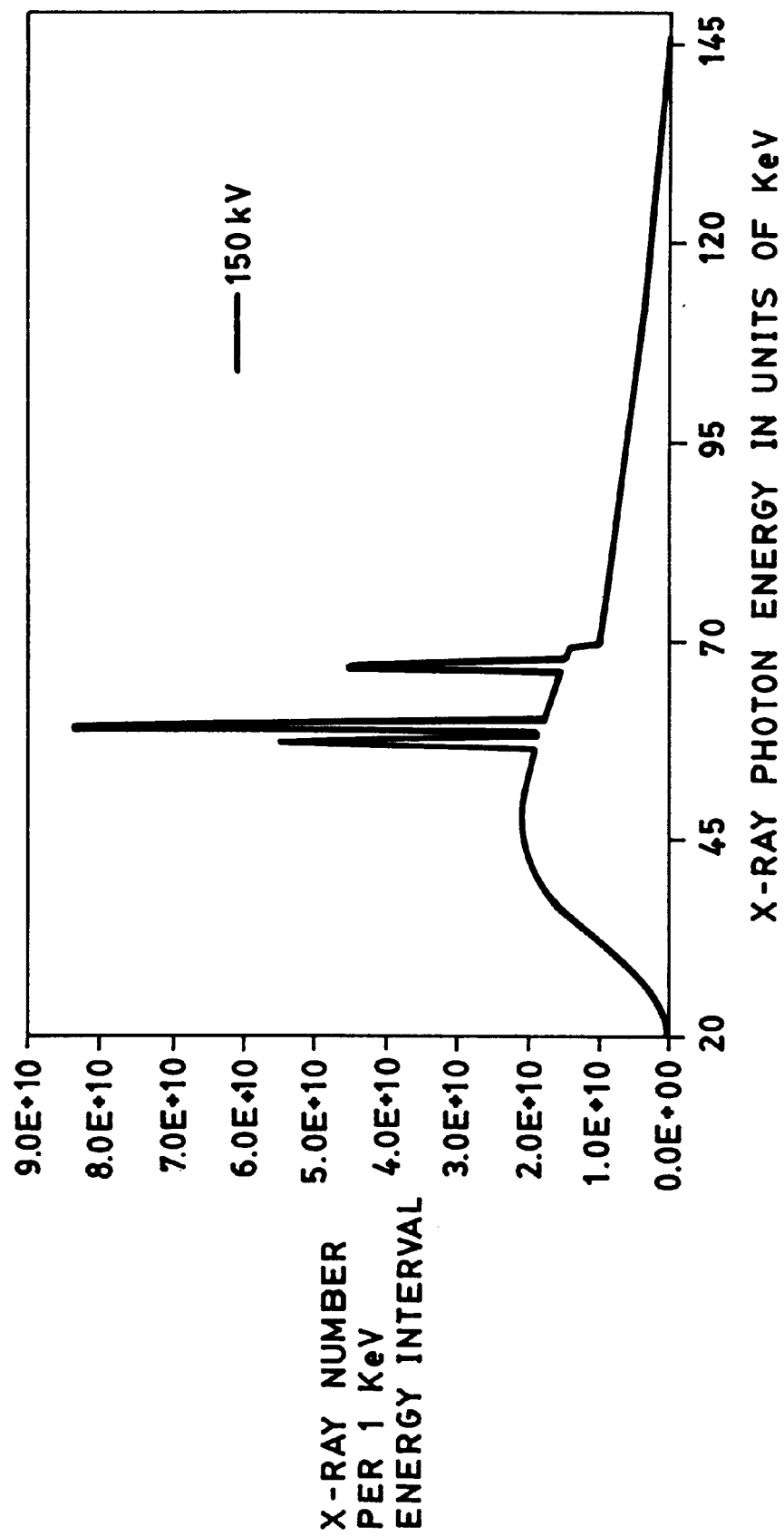

The x-ray source has an energy spectrum covering a broad energy range. In addition to the continuous bremstrahlung spectrum, the energy spectrum may also contain discrete line structure when the high voltage value is high enough, as shown in FIG. 2b. Currently, there is no effective method for providing mono-energetic x-rays for medical imaging. Therefore, all quantitative calculations must be carried out with an x-ray energy that covers a broad energy range. This has been one of the most important tasks in quantitative x-ray imaging. The x-ray source 14 is essentially a point source, meaning that the x-rays appear to be emanating from a single point rather than from a larger area. A portion of the x-rays 32 passes through the subject 12 directly to the front detector assembly 16 without a change in their direction of propagation. These x-rays 32 are called the primary x-rays and convey true information about the subject 12. The remainder of the x-rays 34 are randomly scattered as a result of interaction with the material of the subject 12. These x-rays 34 are called scatter and cause a distortion of the true information.

The front detector 16 contains a large number of individual detector cells in a two-dimensional array. Although the present invention is not limited to a particular type of x-ray detector array, there are two basic types. The first uses thin film amorphous silicon as photodetection medium. The amorphous silicon film has a typical thickness of 1 micrometer ($\mu$m) and is sensitive to visible light. The electric charge induced by visible photons is collected by an array of electrodes. A scintillation screen, which is the x-ray sensitive medium, is placed in close contact with the entire photosensitive area of the photodetector array. X-rays cause the generation of visible photons in the scintillation screen, which are then detected by the amorphous silicon photodetector array, inducing an electric charge proportional to the x-ray energy absorbed in the screen. This type of x-ray detector array is called an external conversion type x-ray detector. Preferably, the detector array has dimensions of 20 centimeters (cm) by 20 cm or 40 cm by 40 cm for a single detector module. A number of such detector modules can be abutted to provide a larger detector. The cell size for this detector array is in the range of from approximately 50 $\mu$m by 50 $\mu$m to approximately 1 mm by 1 mm.

A second type of detector array uses a semiconductor material with a medium high atomic number Z, such as an amorphous selenium film, selenium alloy film, CdZnTe film, or other amorphous or polycrystalline semiconductor films as the x-ray sensitive medium. The charge induced by x-rays directly in the detection medium is collected by an array of electrodes and is proportional to the energy of the x-rays striking the film. The typical thickness of the selenium film is in the range of from approximately 100 $\mu$m to approximately 800 $\mu$m. This type of x-ray detector array is called an internal conversion type x-ray detector. A typical amorphous selenium or selenium alloy detector array module has dimensions of 20 cm by 20 cm or 40 cm by 40 cm with a cell size of from approximately 50 $\mu$m by 50 $\mu$m to approximately 1 mm by 1 mm. A number of such detector modules can be abutted to create a larger detector array.

Other typical two-dimensional detector arrays include charge-couple device (CCD) detectors, CMOS detectors, thin-film thallium-bromide-based detector arrays, avalanche silicon detector arrays, and phosphor-stimulatable computed radiography screens.

The cells of the front detector assembly 16 have variations in their response characteristics. However, these variations are slight and can be normalized, so it is assumed that after normalization, all detector cells in the detector have the same response characteristics.

The combination of signals from all of the cells conveys an image of the x-ray intensity over the area of the front detector 16. Because the detector cells cannot distinguish between primary x-rays 32 and scatter 34, the front detector 16 conveys an image that is a combination of the primary x-rays 32 and the scatter 34, and is denoted by $$D_{fh}(x,y) = D_{fph}(x,y) + D_{fsh}(x,y) \quad (1)$$

where $D_f$ denotes an image in the front detector 16 and (x,y) denotes the two-dimensional Cartesian coordinates of a cell of the front detector 16. For example, when the front detector 16 has a 1024-cell square matrix, x and y will each have integer values in the range of from 1 to 1024, inclusive. $D_{fph}(x,y)$ denotes the contribution from the primary x-rays 32 and $D_{fsh}(x,y)$ denotes the contribution from the scatter 34.

The present invention uses a beam selection means for physically separating primary x-rays from scatter x-rays. The beam selector is sandwiched between the front detector assembly 16 and the rear detector assembly 26, blocking substantially the passage of all of the primary x-rays 32 from the image subject to a number of locations on the x-ray-sensitive medium of the rear detector assembly 26, and permitting the passage of the scatter x-rays 34 to those locations. A preferred embodiment of the x-ray beam selector 18 is an array of cylindrical shapes 20 composed of x-ray-absorbent material and supported by a thin plastic sheet 22 having negligible x-ray absorption. The cylinders 20 are fabricated such that their axes are aligned with the travel direction of the primary x-rays 32. As a result, the cylinders 20, within their cross-sectional area, block all x-rays coming directly from the x-ray source 14. Thus, each cylinder 20 produces a "shadowed" location on the x-ray sensitive medium of the rear detector assembly 26 where the signal of the primary x-rays is essentially zero, while the scatter signals are essentially unaffected. On the other hand, because the cylinders 20 always have a finite size, a small portion of the scatter from the image subject 12 is still reduced at the shadowed locations and at other locations of the rear detector 26. However, as long as the cylinder size 20 is small, this portion of the scatter 34 can be controlled to be negligibly small or can be approximately compensated through calibration. The cross-sectional shape of the cylinders 20 is not important, but for ease in manufacturing, they are preferably round or square. The size of a single cylinder in the beam selector 20 is generally much larger than the size of a single detector cell. Preferably, the cross-section of the cylinders 20 is as small as possible, but for ease in alignment, and because the x-ray sources have a finite size, the cylinders 20 are chosen to have a diameter that is in the range of approximately from 1 mm to 10 mm. If the cylinders 20 are too large, too much scatter 34 would be prevented from reaching the rear detector assembly 26. Preferably, there are as many cylinders as possible in the beam selector 18. The more cylinders 20 there are in the beam selector 18, the greater the accuracy of the measurement at the rear detector 26. A compromise based on these factors results in a pitch that is preferably between 2 mm and 50 mm.

The cylinders 20 are fabricated such that their axes are aligned with the direction of the travel of the primary x-rays 32, which means that the cylinders 20 are not exactly parallel to each other, but are radial to the x-ray source 14. As the x-ray source 14 is located farther away from the beam selector 18, the cylinders 20 approach being parallel to each other. Preferably, the x-ray source 14 is located between 20 cm and 150 cm from the rear surface 24 of the beam selector 18. The invention holds equally true when the x-ray source has a finite size.

The material of the beam selector 18 must ensure that substantially all primary x-rays 32 are absorbed in the shadowed area, and the cylinder material does not produce any secondary x-ray emission or cause any additional scattering. To meet these requirements, chemical elements with medium atomic number Z are preferred, for example, materials with Z between 20 and 34. The cylinders can also have a multilayer structure, with a high-Z material in the core and a medium-Z material outside. The high-Z material absorbs x-rays most efficiently and any secondary x-ray emissions from the core material are efficiently absorbed by the outside layer without inducing further secondary emissions.

The beam selector 18 has approximately the same area as the front detector 16. The distance between the front detector and the rear detector assembly is preferably between 1 cm and 10 cm. The thickness or the height of the cylinders is dependent upon the x-ray energy, where higher energy requires thicker cylinders. In lower energy x-ray imaging, for example, in mammography, the cylinders can actually become thin disks.

There may also be scatter x-rays from the sources other than the image subject 12, such as, for example, from the wall or floor of the building material. These scatter x-rays are excluded by using conventional methods.

Preferably, the rear detector cells are arranged in a rectangular matrix with from 8 to 1,024 cells on a side, where each cell is identified by the general two-dimensional coordinate (I,J). The image received by the rear detector assembly 26 contains two subsets of data, the first being scatter x-ray signals at the shadowed locations. These locations are identified by (i',j'). The second subset of data includes a combination of primary and scatter x-rays at the nonshadowed locations. These locations are identified by (i,j).

In the present invention, these two data subsets are used to derive a low-resolution primary x-ray image data at the rear detector at selected locations. The procedures for the derivation are described below. The term "selected location" is defined as an array of locations on the rear detector 28, where, due to the function of the beam selector 18 and to the use of the procedures of the present invention, the signals contain only derived primary x-rays. This definition of "selected location" ensures consistency between the present application and its antecedent applications.

Figure 1A:
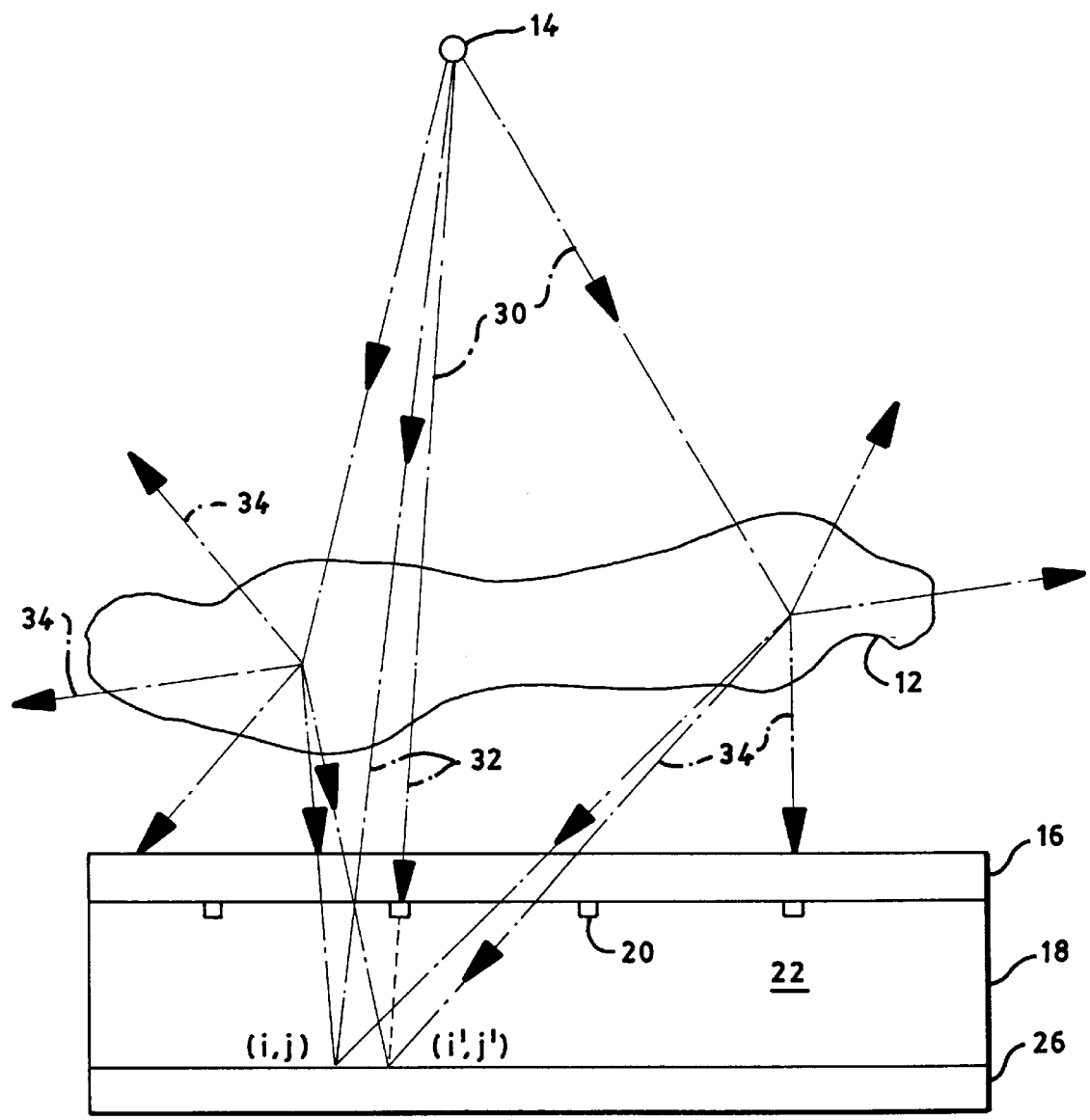
FIGS. 1a and 1b are two-dimensional and three-dimensional diagrams, respectively, for describing the definitions and notations of the present invention.
Figure 1B:
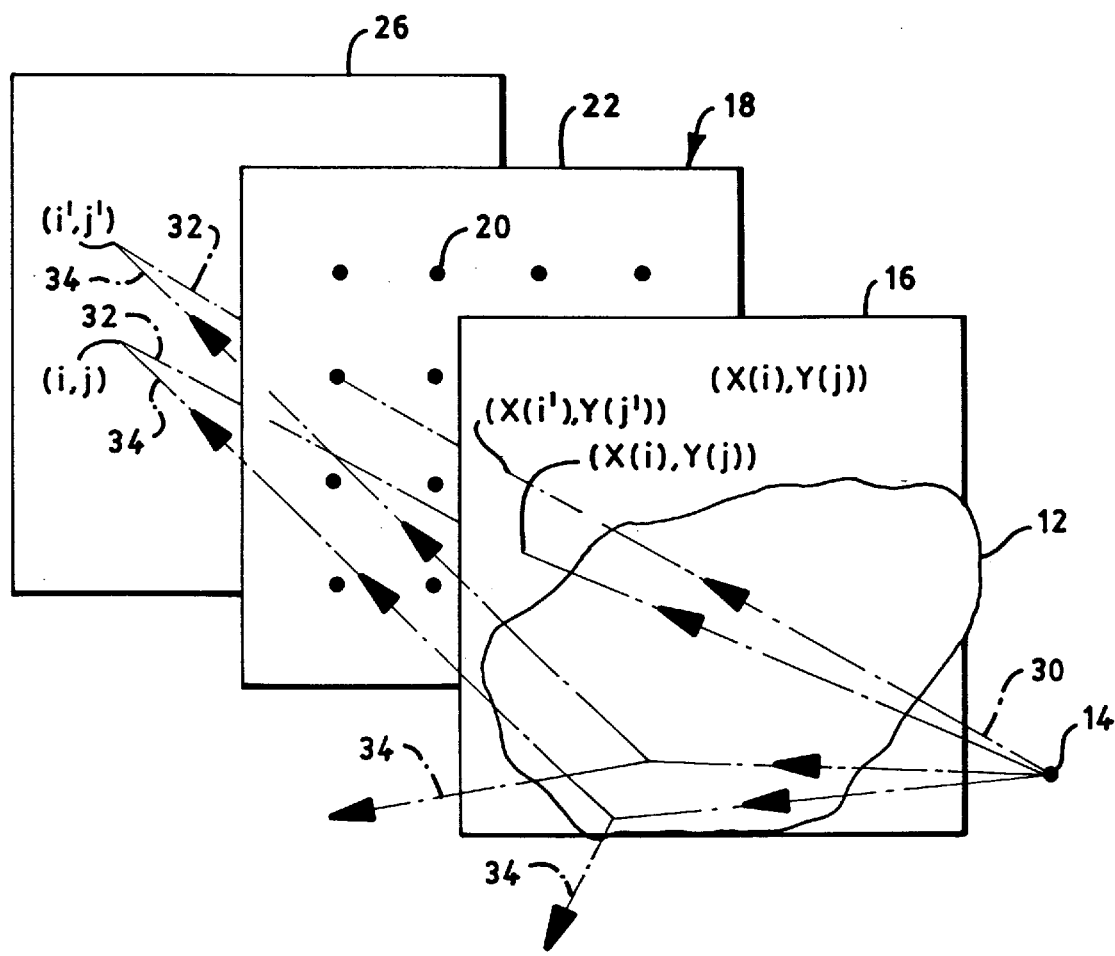

The rear detector cells at the selected locations have a fixed geometric relation with some of the front detector cells. This relation is established by drawing a selected projection line from the x-ray source 14 through the beam selector 18 to the selected location. As shown in FIGS. 1a and 1b, this selected projection line intersects the rear detector surface at a rear detector cell at a coordinate (i,j), and intersects the front detector surface at a front detector cell at a coordinate (x(i),y(j)). Here (x(i),y(j)) denotes the coordinate (x,y) of the front detector cell closest to the selected projection line. An image file $D_{rl}(i,j)$ at the selected locations is a low-resolution image file. The data at the image pixel (i,j) is the data obtained either from a single detector cell or from a combination of a small number of detector cells around the selected projection line. Similarly, $D_{fl}(x(i), y(j))$ denotes an image file from the front detector 26 having a low spatial resolution. Hereinafter, the word "resolution" is used only to represent spatial resolution, as opposed to amplitude resolution. The data at the image location (x(i),y(j)) is the data either of a single detector cell or of a combination of a small number of detector cells around the selected projection line. The relationship between (i,j) and (x(i),y(j)) is experimentally established and stored. The image data on the selected projection lines are low-resolution images and are represented by the subscript lower-case l. The image data from all the front detector cells are high-resolution images and are represented by the subscript lower-case h.

In connection with the material composition of the image subject, four quantities are defined. b(i,j) and s(i,j) are defined as low-resolution images for the selected projection mass densities along the selected projection line (i,j). b(x,y) and s(x,y) are defined as the projection mass densities along the projection line (x,y). The "projection mass density" is defined as the integrated total mass of the image subject along the projection line per unit area. Because the projection mass density is not dependent on the size of detector cells, b(x(i),y(j))=b(i,j) and s(x(i),y(j))=s(i,j).

Figure 3:
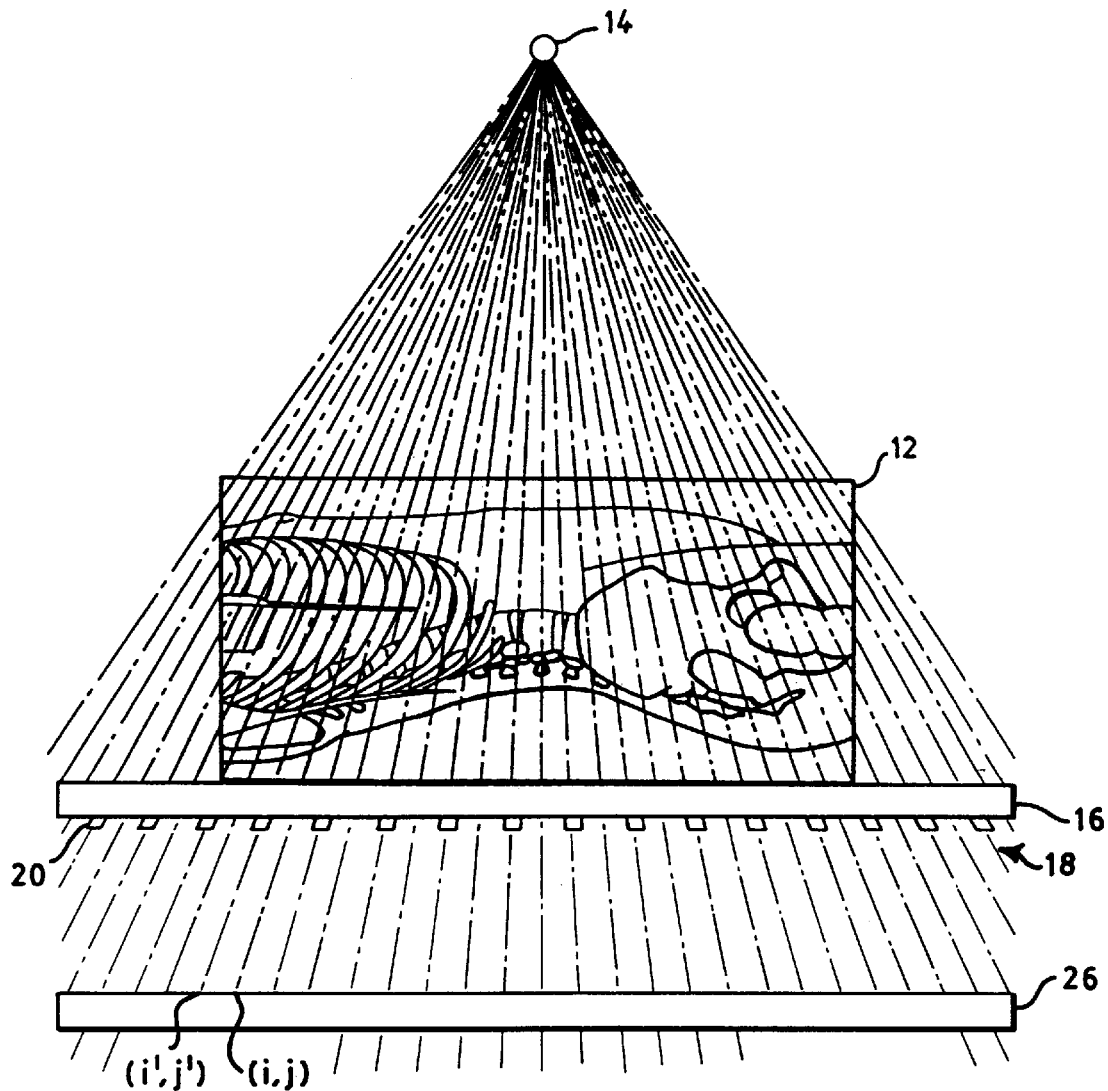
FIG. 3 is a diagram of the first embodiment of the present invention.
Figure 4:
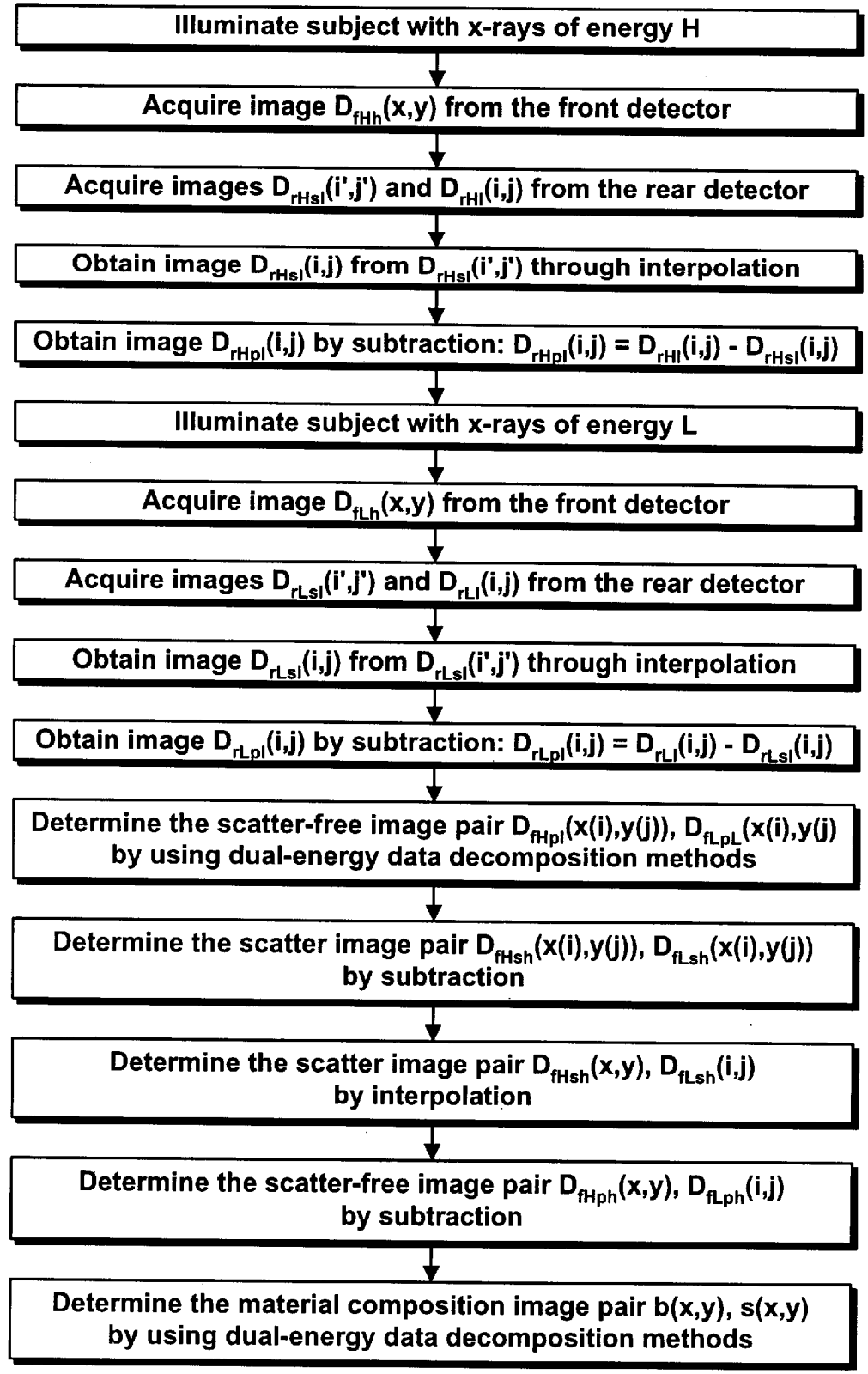
FIG. 4 is a flow diagram of the basic procedures using the dual-energy data decomposition method and the hardware of FIG. 3.

The mathematical and physical foundations of the dual-energy imaging procedures of the present invention are detailed as follows for the preferred embodiment:

As shown in FIG. 3 for the first preferred embodiment, following a high-energy x-ray pulse at an average energy level H and a low-energy pulse at an average energy level L, two images of the rear detector are acquired. The coordinates in each of these two images have a general notation (I,J), with I=1,2,3, ... N and J=1,2,3, ... M, where M and N are integers. (I,J) has two subsets, (i,j) and (i',j'). The data subset at (i',j') is the scatter-only x-ray signals identified as $D_{rHsl}(i',j')$ and $D_{rLsl}(i',j')$. The data subset at (i,j) has a combination of primary x-ray signals and scatter x-ray signals identified as $D_{rHl}(i,j)$ and $D_{rLl}(i,j)$. The locations (i,j) are selected to uniformly cover the entire image plane of the rear detector and close to the locations (i',j'). Because images $D_{rHsl}(i',j')$ and $D_{rLsl}(i',j')$ are both scatter-only x-ray signals, they can be extended to the entire image plane of the rear detector by interpolation. The interpolation does not cause nonnegligible error because of the physical nature of the scatter x-rays. The scatter 34 is essentially caused by Compton scattering, which has a substantially uniform angular distribution in the preferred x-ray energy range. Both empirical data and theoretical calculations show that scatter always has a substantially smooth distribution on a two-dimensional image plane. This means that the change in scatter intensity between adjacent cells is small and smooth. Thus, as long as there are a sufficiently large number of data points, the error incurred due to interpolation is negligible in comparison with other error sources, such as statistical fluctuations of x-ray photon numbers. So, scatter-only signals at the selected location (i,j) are obtained by interpolation, and identified as $D_{rHsl}(i,j)$, and $D_{rLsl}(i,j)$. Accordingly, a pair of primary image signals $D_{rHpl}(i,j)$ and $D_{rLpl}(i,j)$ can be calculated as $$D_{rHpl}(i,j) = D_{rHl}(i,j) - D_{rHsl}(i,j) \tag{2a}$$

$$D_{rLpl}(i,j) = D_{rLl}(i,j) - D_{rLsl}(i,j) \tag{2b}$$

where $D_{rHl}(i,j)$ and $D_{rLpl}(i,j)$ are the directly acquired data and $D_{rHsl}(i,j)$ and $D_{rLsl}(i,j)$ are the interpolated data.

The next step is to calculate the primary images at the front detector from the primary image pair $D_{rHpl}(i,j)$, and $D_{rLpl}(i,j)$. As shown in FIG. 3, the high-resolution image $D_{fHh}(x,y)$ is acquired from the front detector 16 following the high-energy x-ray pulse at an average energy level H. The high-resolution image $D_{fLh}(x,y)$ is acquired from the front detector 16 following the low-energy x-ray pulse at an average energy level L. The high-resolution image pair of the front detector 16 can be written as $$D_{fHh}(x, y) = \int [\Phi_{OH}(E) \times \exp(-(\mu_b(E) \times b(x, y) + \mu_s(E) \times s(x, y))] \times S_f(E) dE + \int \Phi_{fS}(E, x, y) \times S_f(E) dE \tag{3a}$$

and $$D_{fLh}(x, y) = \int [\Phi_{OL}(E) \times \exp(-(\mu_b(E) \times b(x, y) + \mu_s(E) \times s(x, y))] \times S_f(E) dE + \int \Phi_{fS}(E, x, y) \times S_f(E) dE \tag{3b}$$

On the other hand, the low-resolution primary images of the rear detector 26 derived from equation pair 2a, 2b can be written as $$D_{rHpl}(i,j) = \int [\Phi_{OH}(E) \times \exp(-(\mu_b(E) \times b(i,j) + \qquad (4a)$$
$$\mu_s(E) \times s(i,j))] \times S_r(E) dE$$

and $$D_{rLpl}(i,j) = \int [\Phi_{OL}(E) \times \exp(-(\mu_b(E) \times b(i,j) + \qquad (4b)$$
$$\mu_s(E) \times s(i,j))] \times S_r(E) dE$$

where the $\Phi_{OH}(E)$ and $\Phi_{OL}(E)$ are the energy spectra of the x-ray source 14 at the higher energy level H and at the lower energy level L. The projection mass density $b(i,j)$ and $s(i,j)$ of the subject 12 are in units of grams/centimeter$^2$ (g/cm$^2$). $\mu_b(E)$ is the mass attenuation coefficient of bone tissue and $\mu_s(E)$ is the mass attenuation coefficient of soft tissue, with both $\mu_b(E)$ and $\mu_s(E)$ expressed in units of centimeter$^2$/gram (cm$^2$/g). Both of these values are known, having been determined experimentally and tabulated many years ago. The term $[\Phi_0(E) \times \exp(-(\mu_b(E) \times b(x,y) + \mu_s(E) \times s(x,y)))]$ is the energy spectrum of the primary x-rays incident on the front detector 16 after passing through the subject 12, where expo () denotes the value e raised to the power specified in the parenthesis. $S_f(E)$ is the x-ray spectral sensitivity (the electrical signal amplitude from the detector as a function of the number of x-rays with energy E after the x-rays passing through the image subject) of the front detector 16. Note that $S_f(E)$ includes not only the x-ray spectral sensitivity of the detector itself, but also the x-ray transmission factor that accounts for the absorption of x-rays between the subject 12 and the front detector 16. Such absorption is due, for example, to the front detector protective case material. The term $\int \Phi_s(E) \times S_f(E) dE$ represents the signal caused by scatter. The exact expression for the scatter is not known because the scattering process is too complicated to model accurately. The coordinate (x,y) corresponds to a front detector cell.

In the equation pair 4a, 4b, the low-resolution dual-energy image pair is comprised of primary signals and is free of scatter distortion. By using the dual-energy data decomposition methods outlined above and described below, the simultaneous equation pair 4a, 4b is solved to find the solutions for the image pair of material composition $b(i,j)$ and $s(i,j)$. Because of the data decomposition method, solving the highly evolved equation system 4a and 4b is actually a computer software operation to produce a pair of $b(i,j)$ and $s(i,j)$ values as output for a given data pair $D_{rHpl}(i,j)$, $D_{rLpl}(i,j)$ as input.

As described above, because the rear detector cell (i,j) and front detector cell (x(i),y(j)) lie on the same selected projection line, the low-resolution front detector primary image pair $D_{fHpl}(x(i),y(j))$, $D_{fLpl}(x(i),y(j))$ can be further determined from the rear detector primary image pair $D_{rHpl}(i,j)$, $D_{rLpl}(i,j)$ by applying the data decomposition method again. Moreover, the front detector scatter image pair $D_{fHsl}(x(i),y(j))$, $D_{fLsl}(x(i),y(j))$ is found by the equations $$D_{fHsl}(x(i),y(j)) = D_{fHl}(x(i),y(j)) - D_{fHpl}(x(i),y(j)) \qquad (5a)$$

and $$D_{fLsl}(x(i),y(j)) = D_{fLl}(x(i),y(j)) - D_{fLpl}(x(i),y(j)) \qquad (5b)$$

The next step consists of interpolating the values for the low-resolution scatter image $D_{fHsl}(x(i),y(j))$ and $D_{fLsl}(x(i),y(j))$ to include those detector cells that are not on selected projection lines, yielding two high-resolution scatter images $D_{fHsh}(x,y)$ and $D_{fLsh}(x,y)$. The interpolation does not cause loss of accuracy because of the nature of the physical scattering process, as described above. Note an important difference between the scatter image and the primary image. While the scatter image can be interpolated because of the nature of scatter, the primary image cannot be interpolated because the primary image changes with the subject 12 from detector cell to detector cell.

Continuing, the high-resolution primary images on the front detector are denoted as $D_{fHph}(x,y)$ and $D_{fLph}(x,y)$ and are $$D_{fHph}(x,y) = D_{fHh}(x,y) - D_{fHsh}(x,y) \qquad (6a)$$

and $$D_{fLph}(x,y) = D_{fLh}(x,y) - D_{fLsh}(x,y) \qquad (6b)$$

The image pair $D_{fHph}(x,y)$, $D_{fLph}(x,y)$ is a pair of dual-energy x-ray images without scatter. This image pair in turn relates to the material composition of the subject by the equations $$D_{fHph}(x,y) = \int [\Phi_{OH}(E) \times \exp(-(\mu_b(E) \times b(x,y) + \qquad (7a)$$
$$\mu_s(E) \times s(x,y))] \times S_f(E) dE$$

and $$D_{fLph}(x,y) = \int [\Phi_{OL}(E) \times \exp(-(\mu_b(E) \times b(x,y) + \qquad (7b)$$
$$\mu_s(E) \times s(x,y))] \times S_f(E) dE$$

Unlike the simultaneous equation system 3a, 3b, the simultaneous equation system 7a, 7b has only primary x-ray signals, free of scatter distortion. This equation pair is the fundamental dual-energy x-ray imaging equation system with the unprecedented feature that scatter radiation has been essentially removed from the two-dimensional detector. In the equation pair 7a, 7b, the values of $D_{fHph}(x,y)$ and $D_{fLph}(x,y)$ are known from the above-described calculations conducted on the image pair $D_{fHh}(x,y)$, $D_{fLh}(x,y)$ directly measured from the front detector 16, and on the images $D_{rHsl}(i',j')$, $D_{rLsl}(i',j')$, $D_{rHl}(i,j)$, and $D_{rLl}(i,j)$ directly measured from the rear detector 26. The unknown values are the two material composition images $b(x,y)$ and $s(x,y)$.

The dual-energy x-ray data decomposition method can be further applied to the equation pair 7a, 7b. As a result, by using the quantitative relationships $b=b(D_H, D_L)$ and $s=s(D_H, D_L)$ provided by the data decomposition method, a pair of high-resolution images $b(x,y)$ and $s(x,y)$ are readily obtained point by point for all front detector cells (x,y). The solution of the two-component material composition images $b(x,y)$ and $s(x,y)$ has a spatial resolution as high as the front detector 16 can provide.

An alternate to the first embodiment substitutes an x-ray source having a switching high-voltage power supply. The switching high-voltage x-ray source generates x-rays continuously, alternating between low-energy x-rays and high-energy x-rays. The switching high-voltage x-ray source can be treated as a repetitive double-pulse x-ray source.

Lo et al. and other journal articles were published regarding use of a beam stop method to reduce scatter effects. Lo et al. used a beam stop array sandwiched between two stimulated phosphor screens to acquire a scatter-only image for the rear screen. There is certain similarity in the detector geometry to the present invention, but the similarity is only superficial. The essential difference between the present invention and Lo et al. are as follows:

(1) Lo et al. uses a single energy method. The scatter-only image acquired at a single x-ray energy spectrum at the rear detector is multiplied by a constant, and then the product image is used as the scatter image of the front detector. Thus, the method of Lo et al. is essentially different from the present invention. According to the mathematical and physical theory of the present invention, as described above, because the x-ray energy spectra have a broad energy distribution, no functional relationship exists between a single image of the front detector and a single image of the rear detector without knowledge of the unknown image subject. When the unknown image subject is included in the calculations, the usefulness of the relationships is very limited. So far, in the prior art, including the articles by Lo et al., there is no method that can establish such a functional relationship without a dependence on the unknown image subjects. The present invention establishes a well-defined functional relationship between the images of the front detector and the images of the rear detector through a pair of dual-energy primary x-ray signals. This situation can be expressed in the following formulas 8a–8f. First, $$D_{fp}(x(i),y(j)) \neq \text{constant} \times D_{rp}(i,j) \tag{8a}$$

This means that any attempt to obtain the primary image of the front detector by multiplying the rear detector image by a calibration constant will not result in a true primary x-ray image of the front detector. The same is true for the scatter x-ray image, that is $$D_{fs}(x(i),y(j)) \neq \text{constant} \times D_{rs}(i,j) \tag{8b}$$

Second, $$D_{fp}(x(i),y(j)) \neq F(D_{rp}(i,j)) \tag{8c}$$

where F represents any defined functional relationship.

This also means that any attempt to obtain the primary image of the front detector by applying any mathematical operation on the image of the rear detector will not result in a true primary x-ray image of the front detector. The same is true for the scatter image, that is $$D_{fs}(x(i),y(j)) \neq F(D_{rs}(i,j)) \tag{8d}$$

The only relationship that the fundamental physical law allows to establish in the first embodiment hardware system is in the following forms:

$$D_{fHp}(x(i),y(j)) = D_{fHp}(D_{rH}(i,j),D_{rL}(i,j)) \tag{8e}$$

$$D_{fLp}(x(i),y(j)) = D_{fLp}(D_{rH}(i,j),D_{rL}(i,j)) \tag{8f}$$

That is, expressed literally, if a dual-energy x-ray imaging is performed, the low-energy primary x-ray image of the front detector has an accurate, rigorous, and unique relationship with the primary image pair of the rear detector (8e). The same is true for the high-energy primary image of the front detector (8f). These relationships are independent of the image subject, and hence can be established through calibrations when there is no image subject present. These relationships are universally true to the entire image on a pixel-by-pixel basis. The data decomposition method of the present invention is the method for quantitatively establishing these relationships. This is one of the most important conclusions of the present invention.

(2) Because of the differences in the theory and in the method between Lo et al. and the present invention, the hardware is also essentially different. The most important specific difference in the hardware is that, according to the first embodiment of the present invention, the x-ray source must be a dual-energy x-ray source, whereas in Lo et al., only a single energy x-ray source is used.

Second Embodiment

Figure 5:
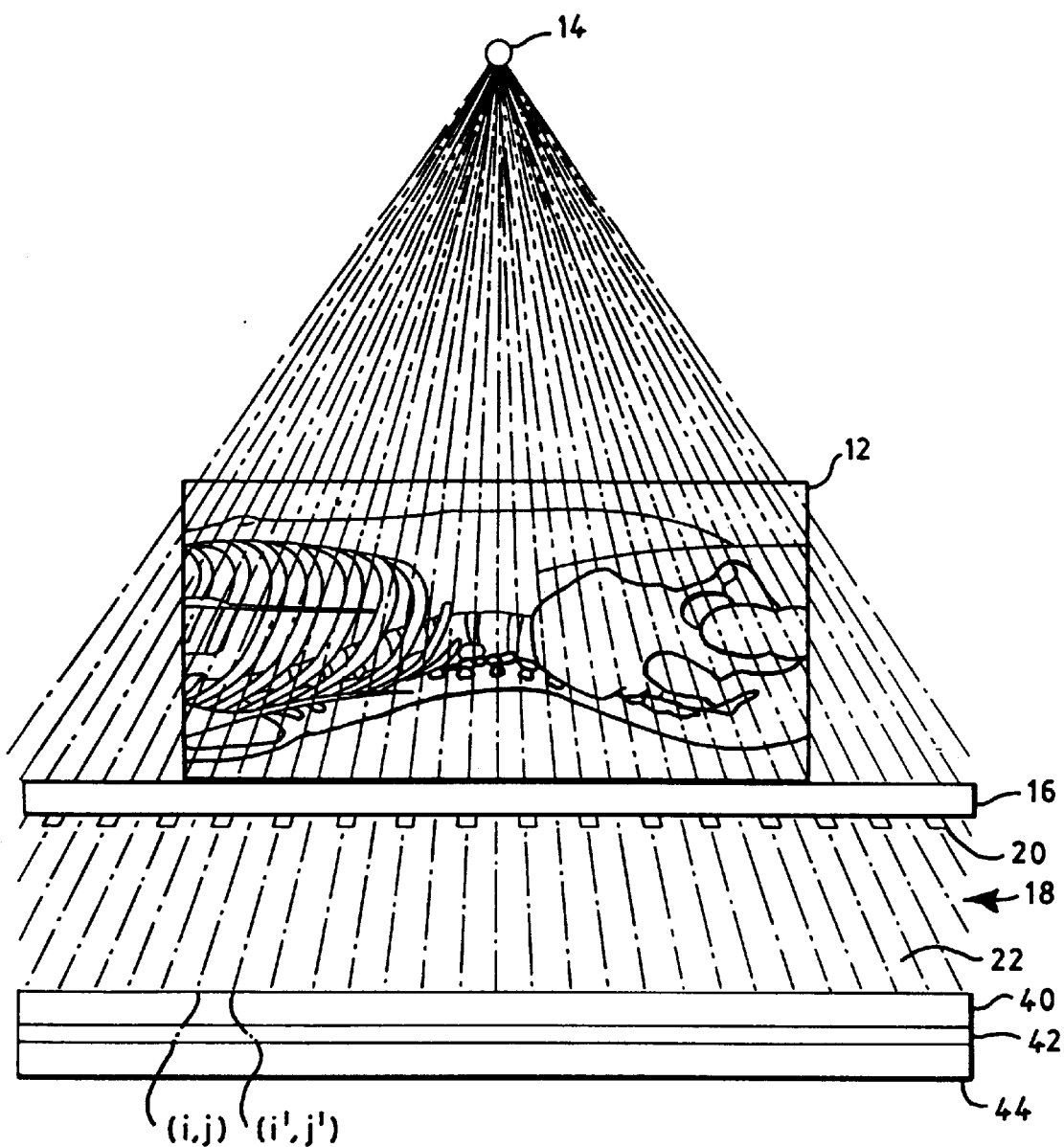
FIG. 5 is a diagram of the second embodiment of the present invention.
Figure 6:
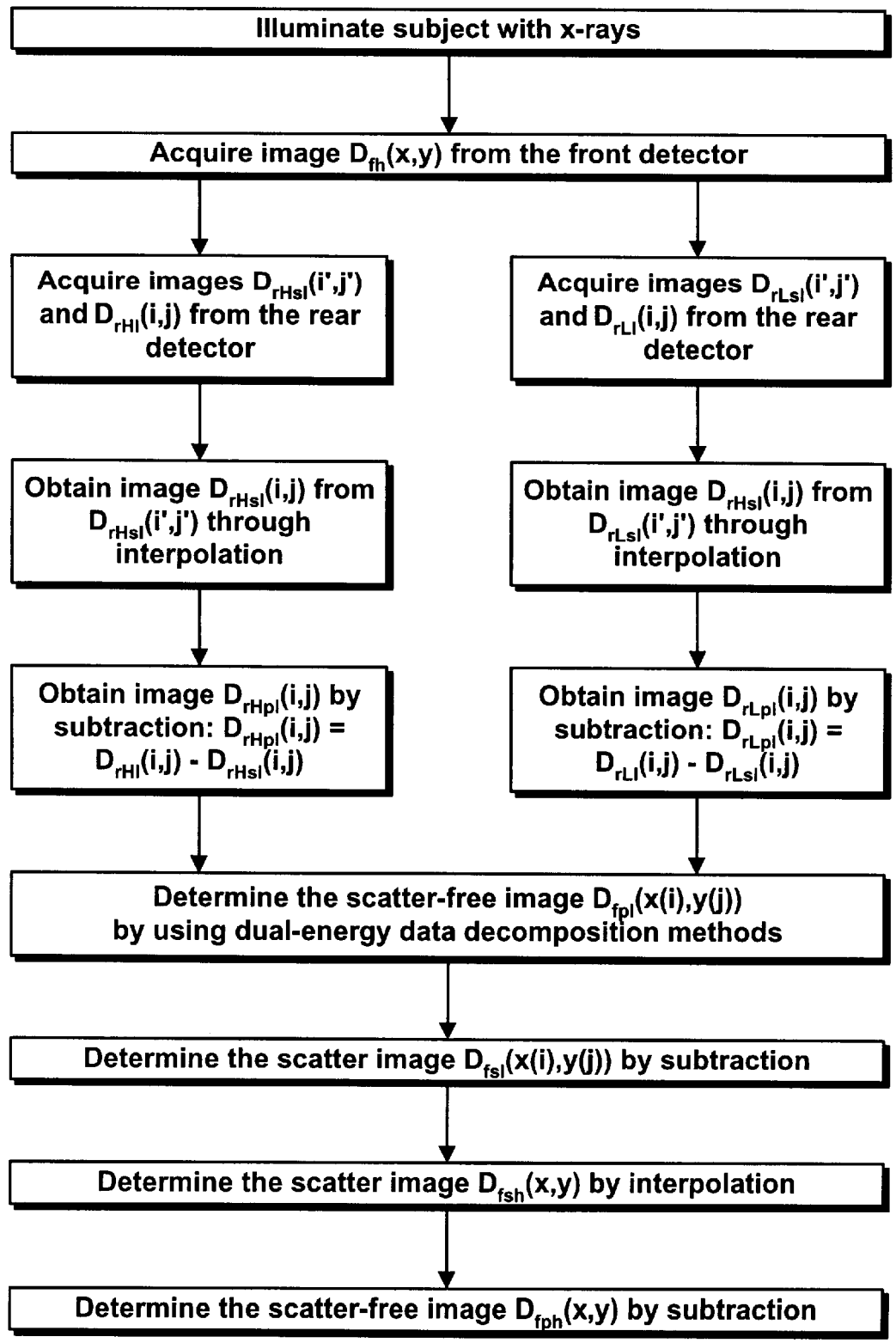
FIG. 6 is a flow diagram of the method of the second embodiment using the hardware of FIG. 5.

In the second embodiment of the apparatus, shown in FIG. 5, the front detector 16 and beam selection means 18 are the same as that of the first embodiment. One difference from the first embodiment is that the x-ray source 14 emits a single-energy spectrum when illuminating the subject. Another difference is that the rear detector assembly 26 is constructed as a dual-energy x-ray imaging detector assembly. It has a low-energy two-dimensional detector 40, an x-ray energy spectral filter 42, and a high-energy two-dimensional detector 44. The filter 42 operates in the conventional manner. It has a transmission function of $\exp(-\mu(E) \times d)$, where E is the energy of the x-rays, $\mu(E)$ is the mass attenuation coefficient of the filter material, and d is the thickness of the filter 42. Because the absorption of x-rays is dependent upon the energy of the x-rays (the mass attenuation coefficient is a function of E), the filter 42 absorbs more of the low-energy x-rays 46 than high-energy x-rays 48. Thus, the proportion of high-energy x-rays 48 to low-energy x-rays 46 after the filter 42 is larger than before the filter 42 and the average normalized x-ray energy after the filter 42 is larger than before the filter 42. Preferably, the low-energy x-rays have an average energy of from 10 keV to 100 keV and high-energy x-rays have an average energy of from 30 keV to 500 keV, with the high-energy x-rays having a higher energy than the low-energy x-rays.

Following x-ray illumination, two images of the rear detector 26 are acquired. The coordinates in each of these two images have a general notation (I,J), with I=1,2,3, . . . N and J=1,2,3, . . . M, where M and N are integers. (I,J) has two subsets of locations, (i,j) and (i',j'). The data set at locations (i',j') is scatter-only x-ray signals identified as $D_{rHs}(i',j')$ and $D_{rLs}(i',j')$. The data set at locations (i,j) has a combination of primary x-ray signals and scatter x-ray signals identified as $D_{rH}(i,j)$ and $D_{rL}(i,j)$. The locations (i,j) are selected to uniformly cover the entire image plane of the rear detector and to be physically close to the locations (i',j'). Because images $D_{rHs}(i',j')$, $D_{rLs}(i',j')$ include only scatter x-ray signals, they can be extended to the entire image plane of the rear detector 26 by interpolation. The interpolation does not cause nonnegligible error, as explained above. So, scatter-only signals at the selected location (i,j) are obtained by interpolation and identified as $D_{rHs}(i,j)$, $D_{rLs}(i,j)$. Accordingly, a pair of primary image signals $D_{rHp}(i,j)$, $D_{rLp}(i,j)$ can be calculated:

$$D_{rHp}(i,j) = D_{rH}(i,j) - D_{rHs}(i,j) \tag{9a}$$

$$D_{rLp}(i,j) = D_{rL}(i,j) - D_{rLs}(i,j) \tag{9b}$$

where $D_{rH}(i,j)$ and $D_{rL}(i,j)$ are the directly acquired data at (i,j) and $D_{rHs}(i,j)$ and $D_{rLs}(i,j)$ are the scatter data interpolated from subset (i',j').

The next step is to calculate the primary images at the front detector from the primary image pair $D_{rHp}(i,i)$, $D_{rLp}(i,j)$. The high-resolution image of the front detector can be written as:

$$D_{fh}(x, y) = \int [\Phi_0(E) \times \exp(-(\mu_b(E) \times b(x, y) + \mu_s(E) \times s(x, y)))] \times S_f(E) dE + \tag{10}$$

-continued $$\int \Phi_S(E) \times S_f(E) dE$$

$\Phi_s(E) \times S_f(E) dE$ represents the signal caused by scatter.

The rear detector assembly 26 has two detectors 40, 44, so there are two low-resolution primary images $D_{rHpl}(i,j)$ and $D_{rLpl}(i,j)$ as derived in (9a) and (9b), which are $$D_{rHpl}(i, j) = \int [\Phi_0(E) \times \exp(-(\mu_b(E) \times b(i, j) + \mu_s(E) \times s(i, j)))] \times S_{rH}(E) dE \quad (11a)$$

and $$D_{rLpl}(i, j) = \int [\Phi_0(E) \times \exp(-(\mu_b(E) \times b(i, j) + \mu_s(E) \times s(i, j)))] \times S_{rL}(E) dE \quad (11b)$$

Note that, as above, $S_{rH}(E)$ and $S_{rL}(E)$ include the x-ray transmission factors that account for the absorption of x-rays between the subject 12 and the respective rear detectors 40, 44. Such absorption for $S_{rH}(E)$ is due, for example, to the front detector assembly 16, the spectral filter 42, the rear detector protective case, and the rear low-energy detector.

Equations 11a and 11b constitute a simultaneous equation system, where the values for the signal pair $D_{rHpl}(i,j)$, $D_{rLpl}(i,j)$ are known quantities. The energy dependent functions $\Phi_0(E) \times S_{rH}(E)$ and $\Phi_0(E) \times S_{rL}(E)$ are not directly known but can be determined in a calibration process. The data decomposition method described below provides a way to determine these quantities in advance of image operations. $b(i,j)$ and $s(i,j)$ are the unknown quantities for which equation pair 11a, 11b must be solved, as described below.

Accurate $b(i,j)$ and $s(i,j)$ are calculated by the data decomposition method of the present invention, as will be described below. Now that the values for $b(i,j)$ and $s(i,j)$ are known, the front low-resolution scatter-free image $D_{fpl}(x,y)$ can be obtained for those front detector cells $(x(i),y(j))$ that are on the selected projection lines by $$D_{fpl}(x(i), y(j)) = \int [\Phi_0(E) \times \exp(-(\mu_b(E) \times b(i, j) + \mu_s(E) \times s(i, j)))] \times S_f(E) dE \quad (12)$$

were the energy dependent function $\Phi_0(E) \times S_f(E)$ is given in calibration, as will be described in the data decomposition section below.

Next, the low-resolution front scatter image $D_{fsl}(x(i),y(j))$ is determined by applying equation 1, $$D_{fsl}(x(i),(j)) = D_{fl}(x(i),y(j)) - D_{fpl}(x(i),y(j))$$

Because of the physical nature of scatter, as described above, the low-resolution scatter image $D_{fsl}(x(i),y(j))$ can be extended to the entire (x,y) plane through interpolation without losing accuracy, yielding the high-resolution scatter image $D_{fsh}(x,y)$, which is then subtracted from the experimentally measured image $D_{fh}(x,y)$, yielding the high-resolution primary image $D_{fph}(x,y)$. In the second embodiment, the dual-energy imaging is performed for the purpose of improving the image quality of the front detector and to remove the scatter from the front detector image.

Data Decomposition Method

The following is a step-by-step description of the data decomposition method summarized above.

The first step is to construct the two simultaneous numerical surface equations $D_H = F_{DH}(b,s)$ and $D_L = F_{DL}(b,s)$ in three-dimensional space. A preferred method to do this is to determine the detection system energy-dependent functions and use these functions to calculate the numerical arrays for $D_H$ and $D_L$.

Note that there is a difference between equation pair 11a, 11b and equation pair 4a, 4b. If a unified notation is used, the two pairs have the same form. The system energy-dependent function of a detector, denoted sps(E), is defined as $$sps(E) = \Phi_0(E) \times S(E) \quad (13)$$

where $\Phi_0(E)$ is the x-ray energy spectrum emitted from the x-ray source 14 and S(E) is the energy response function of the detector. In the first embodiment, the equation pair 4a, 4b becomes $$sps_H(E) = \Phi_{0H}(E) \times S_f(E) \quad (14a)$$

and $$sps_L(E) = \Phi_{0L}(E) \times S_f(E) \quad (14b)$$

and in the second embodiment, the equation pair 11a, 11b becomes $$sps_H(E) = \Phi_0(E) \times S_{fH}(E) \quad (15a)$$

and $$sps_L(E) = \Phi_0(E) \times S_{fL}(E) \quad (15b)$$

The function sps(E) contains the complete energy-dependent features of the dual-energy imaging system. The advantage of determining sps(E) is that all subsequent data processing methods are made independent of the subject 12.

A preferred method for determining the energy-dependent function sps(E) of the imaging system is to use the well-established absorption method. An absorption curve is measured by using a collimated narrow primary x-ray beam. An absorption plate composed of a known material, such as aluminum, Lucite®, or copper, is placed between the x-ray source and the detector. The electrical signal from a single detector cell D(t) as a function of the absorption plate thickness t is experimentally determined and is related to sps(E) through the equation $$D(t) = \int sps(E) \times \exp(-\mu(E) \times t) dE \quad (16)$$

Since the mass attenuation coefficient $\mu(E)$ of the absorption plate material is known, the function sps(E) can be determined to the accuracy required by the dual-energy x-ray imaging. This method is especially convenient for the internal conversion type of two-dimensional x-ray detectors. In these detectors, the detection efficiency and detector energy response function can be expressed in a simple analytical expression with few unknown parameters to be solved. The energy response function for internal conversion type of detectors is written as $$S(E) = S_0(E) \times S_1(E) \quad (17a)$$

or $$S(E) = \{[1 - \exp(-\mu_0(E) \times d)] \times \alpha E\} \times \exp(-\mu_1(E) \times d_1 - \mu_2(E) \times d_2) \quad (17b)$$

where $S_0(E) = [1-\exp(-\mu_0(E) \times d)] \times \alpha E$ is the electrical signal amplitude induced by x-ray photons with energy E, $\mu_0(E)$ is the mass attenuation coefficient of the detector's conversion layer, d is the thickness of the conversion layer of the detector cell, and where $S_1(E)=\exp(-\mu_1(E)\times d_1-\mu_2(E)\times d_2)$ is the x-ray transmission after leaving the image subject to the detector surface, $\mu_1(E)$ and $\mu_2(E)$ are the attenuation coefficients of two given materials, and $d_1$ and $d_2$ are the thickness values of these materials.

When the x-ray energy spectrum $\Phi_0(E)$ is separately measured, these unknown parameters $\alpha$, d, $d_1$, and $d_2$ are determined by using standard least square parameter-fitting techniques through equation 16. Then, the energy-dependent function sps(E) is obtained to a high degree of accuracy for a single cell. After normalization, the energy dependent function sps(E) of one cell represents that of all the cells of the same detector.

Once the value for sps(E) is determined to the desired accuracy, the dual-energy signals as a function of the material composition of the subject are calculated through the equations $$D_H=\int sps_H(E)\times\exp(-(\mu_b(E)\times b+\mu_s(E)\times s))dE \quad (18a)$$

and $$D_L=\int sps_L(E)\times\exp(-(\mu_b(E)\times b+\mu_s(E)\times s))dE \quad (18b)$$

where $\mu_b(E)$ and $\mu_s(E)$ are the well-documented mass attenuation coefficients for bone tissue and soft tissue, respectively. The mass surface densities b and s are assigned values that sufficiently cover the real range of the subject 12.

Another preferred method for constructing the quantitative explicit functions $D_H=F_{DH}(b,s)$ and $D_L=F_{DL}(b,s)$ is to conduct direct measurements of signals $D_H$ and $D_L$ at a number of selected b and s values. The number of data points for b and s is in the range of approximately 5 to approximately 30. The more data points that are used, the higher the accuracy of the results. However, the number of data points is limited by the acceptable amount of work. The entire functions $D_H=F_{DH}(b,s)$ and $D_L=F_{DL}(b,s)$ are obtained from the directly measured data points by using standard two-dimensional interpolation algorithms. After interpolation, there are from approximately 50 to approximately 50,000 data points for b and s. The interpolation in this case is valid because the functions $D_H=F_{DH}(b,s)$ and $D_L=F_{DL}(b,s)$ are continuous, smooth, and monotonous.

Figure 7A:
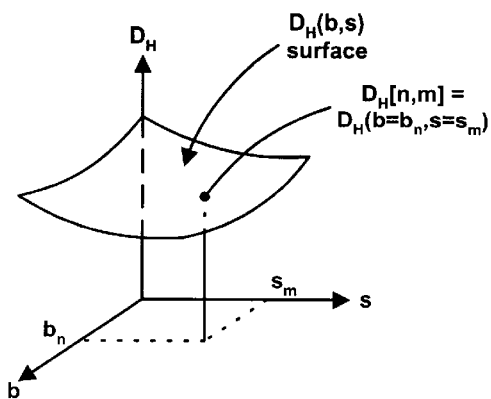
FIGS. 7a to 7d are a graphical representation of a method for inverting the nonlinear dual-energy equation systems.
Figure 7B:
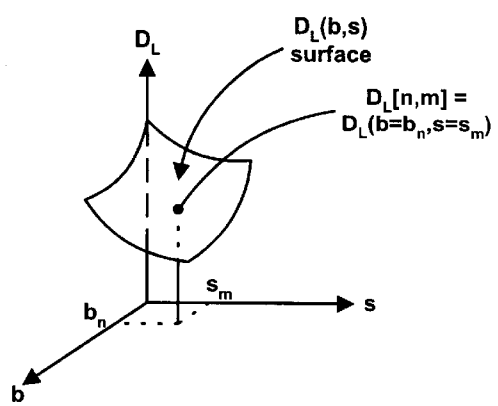
Figure 7C:
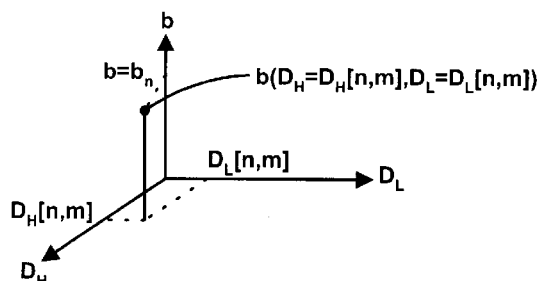
Figure 7D:
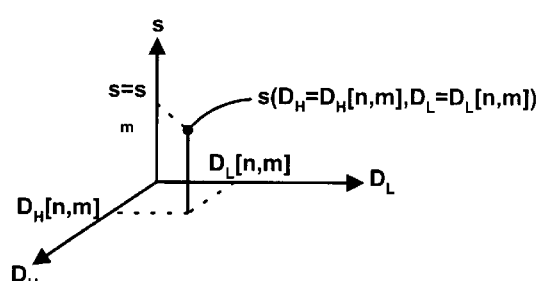

The second step is to determine the material composition images b and s as functions of the image pair $D_H$, $D_L$. The procedures for obtaining a simultaneous equation system for b($D_H$, $D_L$) and s($D_H$, $D_L$) are shown graphically in FIGS. 7a to 7d. To do so, the simultaneous equation pair $D_H=F_{DH}(b,s)$ and $D_L=F_{DL}(b,s)$ must be inverted. A preferred method of inversion is as follows: (1) as in FIGS. 7a and 7b, assign a pair of values in the desired range to b and s corresponding to one of the coordinate points in the (b,s) plane so that b=bn, and s=$s_m$, where n=0,1,2, . . . , N, and m=0,1,2, . . . , M. Typical N and M values are in the range of between approximately 50 and approximately 5,000. The larger N and M, the higher the accuracy of the results. However, the largest values for N and M are limited by the available capacity of computer memory and computing speed. From the two numerical equations representing the three-dimensional surfaces $F_{DL}(b,s)$ and $F_{DH}(b,s)$, determine a pair of $D_H$ and $D_L$ values so that $D_H[n,m]=D_H(b=b_n, s=s_m)$ and $D_L[n,m]=D_L(b=b_n, s=s_m)$, where $D_H[n,m]$ and $D_L[n,m]$ are two specific real numbers, and (2) as in FIGS. 7c and 7d, replot the four numbers $D_H[n,m]$, $D_L[n,m]$, $b_n$, and $s_m$ to provide a pair of data points on the three-dimensional surfaces b($D_H$, $D_L$) and s($D_H$, $D_L$). The data point on the three-dimensional surface b($D_H$, $D_L$) is $D_H=D_H[n,m]$, $D_L=D_L[n,m]$, b=$b_n$, and the data point on the three-dimensional surface s($D_H$, $D_L$) is $D_H=D_H[n,m]$, $D_L=D_L[n, m]$, s=$s_m$. After going through all the b=$b_n$ values ($b_0,b_1,b_2,\ldots,b_N$) and all the s=$s_m$ values ($s_0, s_1, s_2, \ldots, s_M$), the essential part of the inversion task is complete. However, for the purpose of storing the inverted arrays b=b($D_H$, $D_L$) and s=s($D_H$, $D_L$), the step sizes of $D_H=D_H[n,m]$ and $D_L=D_L[n,m]$ must be adjusted. In the inverted space, $D_H$ and $D_L$ are basis coordinates. From the N×M data points, only J data points are selected for $D_H$ and only K data points are selected for $D_L$, where J and K are approximately in the same range as N and M. In the final form after the second step, two two-dimensional arrays are obtained and stored: b=b($D_H$, $D_L$) and s=s($D_H$, $D_L$), where $D_H=D_H[j]$, $D_L=D_L[k]$; j=0,1,2, . . . , J, $D_H[j]>D_H[j+1]$ and k=0,1,2, . . . , K, $D_L[k]>D_L[k+1]$. Two additional one-dimensional arrays $D_H[j]$ and $D_L[k]$ are also stored. Arrays $D_H[j]$ and $D_L[k]$ are saved so that accuracy as high as real number calculations can provide is maintained.

Note the important theoretical foundation for the numerical inversion process. It can be generally proven, using mathematics and physics arguments, that under reasonable dual-energy imaging conditions, a unique solution that corresponds to true physical reality always exists. The most important feature used for the mathematical proof consists in the fact that each equation in the dual-energy fundamental equation system in its original form is continuous, continuous for their derivatives up to any high order, and uniformly monotonous with respect to both variables b and s. Because of the uniqueness of the solution, the above inversion process is meaningful and always gives a correct solution.

The third step is to find the desired results from the input data according to the established equations. The desired values for b and s at each cell location is determined by inserting the available data pair ($D_H$, $D_L$) into the numerical equations of step 2. Conversely, the desired values for $D_H$, $D_L$, or only one of them if only one is needed, at each discrete cell location is determined by inserting the available data pair (b,s) into the numerical equations of step 1.

The final step is to maintain the accuracy of the values for b and s in order to maintain a continuous domain function. This means that the accuracy of the calculations is maintained at a level as high as the result that would be given by real number analytical calculations. Because of the digital nature of computers, the data arrays stored in computers must have finite steps, which are assumed here to have integer values as indices of the real number arrays. The following procedures ensure elimination of the errors in connection with these finite steps in data processing.

In step 1, in the process of constructing the equation pair for $D_H[n,m]=D_H(b=b_n, s=s_m)$ and $D_L[n,m]=D_L(b=b_n, s=s_m)$, for each pair of values of $b_n$ and $s_m$, the $D_H[n,m]$ and $D_L[n,m]$ are measured or calculated to an accuracy of real numbers. $D_H[n,m]$ and $D_L[n,m]$ are stored in computer as real number arrays.

In step 2, the inversion process, including replotting in $D_H$ space and $D_L$ space, introduces no errors due to the data processing. The step sizes can be changed without losing any accuracy as long as values for $D_H=D_H[j]$ are selected that are exactly equal to one of the $D_H[n,m]$ values that satisfies the condition $D_H[j-1]>D_H[j]>D_H[j+1]$, and values for $D_L=D_L[k]$ are selected that are exactly equal to one of the $D_L[n,m]$ values that satisfies the condition $D_L[k-1]>D_L[k]>D_L[k+1]$.

In step 3, for each measured dual-energy signal data pair ($D_{HEX}$, $D_{LEX}$), find out the closest j and k values according to the criteria: $D_H[j] \geq D_{HEX} \geq D_H[j+1]$ and $D_L[k]$ $\geq D_{LEX} \geq D_L[k+1]$. From the index values j and k, the closest b and s are first determined as $b_0 = b_0(D_H[j], D_L[k])$ and $s_0 = s_0(D_H[j], D_L[k])$. The following equations give b and s values to an accuracy as high as real number calculations can provide $$b = b_0(D_H[j], D_L[k]) + \qquad (19a)$$
$$[\partial b(D_H, D_L)/\partial D_H]_{D_H=D_H[j];D_L=D_L[k]} \times$$
$$(D_{HEX} - D_H[j]) +$$
$$[\partial b(D_H, D_L)/\partial D_L]_{D_H=D_H[j];D_L=D_L[k]} \times$$
$$(D_{LEX} - D_L[k]) + \text{higher order terms}$$

and $$s = s_0(D_H[j], D_L[k]) + \qquad (19b)$$
$$[\partial s(D_H, D_L)/\partial D_H]_{D_H=D_H[j];D_L=D_L[k]} \times$$
$$(D_{HEX} - D_H[j]) +$$
$$[\partial s(D_H, D_L)/\partial D_L]_{D_H=D_H[j];D_L=D_L[k]} \times$$
$$(D_{LEX} - D_L[k]) + \text{higher order terms}$$

higher order terms where the values for the higher order terms are found in standard calculus textbooks.

Also in step 3, if the image pair $D_L$ and $D_H$ from a given material composition data pair $(b_{ex}, s_{ex})$ is to be found, $D_H$ and $D_L$ are obtained to an accuracy of real numbers by using similar standard Taylor expressions.

Thus, the procedures described above provide methods for directly solving the nonlinear dual-energy x-ray imaging fundamental equation systems in its original form with reasonably selected x-ray energy spectra at an accuracy as high as using real number analytical calculations can provide.

The following is a list of contemplated variations in the embodiments:

(1) According to current theory, in terms of interaction with x-rays, a broad range of image subjects with a material composition at low to medium atomic numbers can be decomposed into a broad range of two materials with different mass attenuation coefficients. For example, the soft tissue of human body can be decomposed into lean tissue and fat tissue by using dual-energy x-ray imaging methods.

(2) The entire process of constructing the $(D_H, D_L)$ pair as functions of (b,s) may be carried out using a functional scale or grid steps other than a linear scale, such as a logarithmic scale.

(3) Some well-established computation tools, such as sorting algorithms or database procedures, can be used to carry out the inversion process described above.

(4) In the procedures described above, in some cases, prior art dual-energy x-ray data decomposition methods can also be used for obtaining the low-resolution front detector image $D_{fpl}$ or image pair $D_{fHpl}$ and $D_{fLpl}$. These methods can be characterized as solving the nonlinear fundamental dual-energy x-ray equation systems through a linearization approximation method with corrections for beam hardening effects. The correction includes second-order approximations. However, in doing so, the results will be limited by the accuracy and capability inherent to these approximation methods used in the process.

(5) All of the steps described above, including the data decomposition method and the scatter elimination method, can be combined together to various degrees, from combining any two steps to combining all the steps into one procedure. For example, in the first embodiment, a four-equation system can be established for calculating $(D_{fHp}, D_{fLp})$ from $(D_{rH}, D_{rL})$ without explicitly determining (b,s). One way of doing so is to construct a pair of quantitative relationships $D_{fHp} = (D_{rH}, D_{rL})$ and $D_{fLp} = (D_{rH}, D_{rL})$ in a data base and storing them. From the measured data pair $(D_{rH}, D_{rL})$ of the rear detector assembly, a new data pair $(D_{fHp}, D_{fLp})$ of the front detector assembly can be directly found.

The foregoing descriptions of the preferred embodiments of the invention have been presented for the purpose of illustration and description. They are not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A dual-energy x-ray imaging system for taking two-dimensional images of a subject, said system comprising:

(a) in physical sequence from front to back, an x-ray source, a front two-dimensional x-ray detector, a beam selection means, and a rear two-dimensional x-ray detector, said subject being located between said x-ray source and said front detector;

(b) said x-ray source being adapted to emit x-rays with two different energy spectra for passage through said subject, said x-rays including primary x-rays having their direction of travel unaltered by interaction with said subject and said x-rays including scatter x-rays having their direction of travel altered by interaction with said subject;

(c) said front detector receiving said primary x-rays and said scatter x-rays;

(d) said rear detector receiving those of said x-rays passed by said beam selection means and having a plurality of selected locations and a plurality of shadowed locations; and (e) said beam selection means preventing passage of said primary x-rays to said shadowed locations, allowing passage of said scatter x-rays to said shadowed locations, and allowing passage of said primary x-rays and said scatter x-rays to said selected locations.

2. The x-ray imaging system of claim 1 wherein said x-ray source is adapted to alternately emit x-ray pulses of said two different energy spectra.

3. The x-ray imaging system of claim 1 wherein one of said energy spectra has an average energy in the range of from approximately 15 keV to approximately 50 keV, and the other of said energy spectra has an average energy in the range of from approximately 20 keV to approximately 250 keV.

4. The x-ray imaging system of claim 1 wherein said front detector array includes a plurality of x-ray-sensitive detector cells arranged in a substantially rectangular matrix with from approximately 128 to approximately 16,384 detector cells on a side.

5. The x-ray imaging system of claim 1 wherein said beam selection means is substantially comprised of an array of cylinders having axes, said cylinders being composed of an x-ray-absorbent material and being supported by a material having negligible x-ray absorption characteristics, said axes being parallel to the direction of travel of said primary x-rays.

6. The x-ray imaging system of claim 5 wherein the thickness of said beam selection means is between approximately 0.5 mm and 5 cm.

7. The x-ray imaging system of claim 5 wherein said cylinders have a diameter of between approximately 1.0 mm and approximately 10 mm, and a pitch of between approximately 2 mm and approximately 50 mm.

8. The x-ray imaging system of claim 1 wherein said rear detector assembly includes a rear detector array having a plurality of x-ray-sensitive detector cells arranged in a substantially rectangular matrix with from approximately 8 to approximately 1,024 detector cells on a side.

9. A dual-energy x-ray imaging system for taking two-dimensional images of a subject, said system comprising:

(a) in physical sequence from front to back, an x-ray source, a front two-dimensional x-ray detector, a beam selection means, and a rear two-dimensional x-ray detector assembly, said subject being located between said x-ray source and said front detector;

(b) said x-ray source being adapted to emit x-rays of a single energy spectrum for passage through said subject, said x-rays including primary x-rays having their direction of travel unaltered by interaction with said subject and said x-rays including scatter x-rays having their direction of travel altered by interaction with said subject;

(c) said front detector receiving said primary x-rays and said scatter x-rays;

(d) said rear detector receiving those of said x-rays passed by said beam selection means and having a plurality of selected locations and a plurality of shadowed locations;

(e) said beam selection means preventing passage of said primary x-rays to said shadowed locations, allowing passage of said scatter x-rays to said shadowed locations, and allowing passage of said primary x-rays and said scatter x-rays to said selected locations; and (f) said rear detector assembly including, in physical sequence from front to back, a low-energy detector, an x-ray energy spectral filter, and a high-energy detector.

10. The x-ray imaging system of claim 9 wherein said energy spectrum has an average energy in the range of from approximately 15 keV to approximately 250 keV.

11. The x-ray imaging system of claim 9 wherein said front detector array includes a plurality of x-ray-sensitive detector cells arranged in a substantially rectangular matrix with from approximately 128 to approximately 16,384 detector cells on a side.

12. The x-ray imaging system of claim 9 wherein said beam selection means is substantially comprised of an array of cylinders having axes, said cylinders being composed of an x-ray-absorbent material and being supported by a material having negligible x-ray absorption characteristics, said axes being parallel to the direction of travel of said primary x-rays.

13. The x-ray imaging system of claim 12 wherein the thickness of said beam selection means is between approximately 0.5 mm and 5 cm.

14. The x-ray imaging system of claim 12 wherein said cylinders have a diameter of between approximately 1.0 mm and approximately 10 mm and a pitch of between approximately 2 mm and approximately 50 mm.

15. The x-ray imaging system of claim 9 wherein said rear low-energy detector includes a plurality of x-ray-sensitive detector cells arranged in a substantially rectangular matrix with from approximately 8 to approximately 1,024 detector cells on a side, said rear high-energy detector including a plurality of x-ray-sensitive detector cells, the arrangement and quantity of said rear high-energy detector cells being substantially the same as the arrangement and quantity of said rear low-energy detector cells.

16. A method for performing dual-energy x-ray imaging of a subject using an imaging system having two-dimensional x-ray detectors, said subject being composed substantially of two materials, $M_A$ and $M_B$, that interact differently with x-rays, said material $M_A$ having a two-dimensional projection mass density A and said material $M_B$ having a two-dimensional projection mass density B, said imaging system including, in physical sequence from front to back, a dual-energy x-ray source, a front two-dimensional x-ray detector having a plurality of front detection locations identified by the notation (x,y), a beam selection means, and a rear two-dimensional x-ray detector having a plurality of selected rear detection locations identified by the notation (i,j) and a plurality of shadowed rear detection locations identified by the notation (i',j'), said selected rear detection locations and said shadowed rear detection locations being mutually exclusive, said subject being between said x-ray source and said front detector, said x-ray source being adapted to emit x-rays at two different average energy levels, H and L, for passage through said subject, said x-rays including primary x-rays having their direction of travel unaltered by interaction with said subject and said x-rays including scatter x-rays having their direction of travel altered by interaction with said subject, said front detector having selected detection locations, identified by the notation (x(i),y(j)), that are intersected by x-ray projection lines extending from said x-ray source to said selected rear detection locations (i,j), said beam selection means permitting passage of said primary x-rays and said scatter x-rays to said selected rear detection locations, preventing passage of said primary x-rays to said shadowed rear detector locations, and allowing passage of said scatter x-rays to said shadowed rear detection locations, said method comprising the steps of:

(a) illuminating said subject with x-rays of said average energy level H;

(b) acquiring a high-resolution image $I_{fHh}$ from said front detection locations (x,y) and processing said image $I_{fHh}$ to normalize it and to subtract dark signals, yielding an image $D_{fHh}(x,y)$ which is composed of said primary x-rays and said scatter x-rays;

(c) producing, from said image $D_{fHh}(x,y)$, a low-resolution image $D_{fHl}(x(i),y(j))$ representing said selected front detection locations (x(i),y(j));

(d) acquiring a low-resolution image $I_{rHl}$ from said selected rear detection locations (i,j) and processing said image $I_{rHl}$ to normalize it and to subtract dark signals, yielding an image $D_{rHl}(i,j)$;

(e) acquiring a low-resolution scatter image $I_{rHsl}$ from said shadowed rear detection locations (i',j') and processing said image $I_{rHsl}$ to normalize it and to subtract dark signals, yielding an image $D_{rHsl}(i',j')$;

(f) illuminating said subject with x-rays of said average energy level L;

(g) acquiring a high-resolution image $I_{fLh}$ from said front detection locations (x,y) and processing said image $I_{fLh}$ to normalize it and to subtract dark signals, yielding an image $D_{fLh}(x,y)$ which is composed of said primary x-rays and said scatter x-rays;

(h) producing, from said image $D_{fLh}(x,y)$, a low-resolution image $D_{fLl}(x(i),y(j))$ representing said selected front detection locations (x(i),y(j));

(i) acquiring a low-resolution image $I_{rLl}$ from said selected rear detection locations (i,j) and processing said image $I_{rLl}$ to normalize it and to subtract dark signals, yielding an image $D_{rLl}$(i,j);

(j) acquiring a low-resolution scatter image $I_{rLsl}$ from said shadowed rear detection locations (i',j') and processing said image $I_{rLsl}$ to normalize it and to subtract dark signals, yielding an image $D_{rLsl}$(i',j');

(k) calculating a low-resolution scatter image $D_{rHsl}$(i,j) by extending said low-resolution scatter image $D_{rHsl}$(i',j') to said selected rear detection locations (i,j) through interpolation and calculating a low-resolution scatter image $D_{rLsl}$(i,j) by extending said low-resolution scatter image $D_{rLsl}$(i',j') to said selected rear detection locations (i,j) through interpolation;

(l) calculating a low-resolution primary x-ray image pair $D_{rHpl}$(i,j) and $D_{rLpl}$(i,j) by subtracting said image $D_{rHsl}$(i,j) from said image $D_{rHl}$(i,j) to yield $D_{rHpl}$(i,j) and subtracting said image $D_{rLsl}$(i,j) from said image $D_{rLl}$(i,j) to yield $D_{rLpl}$(i,j);

(m) calculating a low-resolution primary x-ray image pair $D_{fHpl}$(x(i),y(j)) and $D_{fLpl}$(x(i),y(j)) from said low-resolution dual-energy primary x-ray image pair $D_{rHpl}$(i,j) and $D_{rLpl}$(i,j);

(n) calculating a low-resolution scatter x-ray image $D_{fHsl}$(x(i),y(j)) by subtracting said image $D_{fHpl}$(x(i),y(j)) from said image $D_{fHl}$(x(i),y(j)) and calculating a low-resolution scatter x-ray image $D_{fLsl}$(x(i),y(j)) by subtracting said image $D_{fLpl}$(x(i),y(j)) from said image $D_{fLl}$(x(i),y(j));

(o) calculating a high-resolution scatter image $D_{fHsh}$(x,y) by extending said low-resolution scatter image $D_{fHsl}$(x(i),y(j)) to the entire image area of said front detector through interpolation and calculating a high-resolution scatter image $D_{fLsh}$(x,y) by extending said low-resolution scatter image $D_{fLsl}$(x(i),y(j)) to said entire image area of said front detector through interpolation;

p) calculating a high-resolution primary x-ray image $D_{fHph}$(x,y) at said front detector by subtracting said image $D_{fHsh}$(x,y) from said image $D_{fHh}$(x,y) and calculating a high-resolution primary x-ray image $D_{fHph}$(x,y) at said front detector by subtracting said image $D_{fLsh}$(x,y) from said image $D_{fLh}$(x,y);

(q) whereby said images $D_{fHph}$(x,y) and $D_{fLph}$(x,y) form a high-resolution, two-dimensional, dual-energy primary x-ray image pair of said subject at said front detector after said scatter x-rays have been substantially eliminated, said image pair having a spatial resolution substantially equal to the highest spatial resolution available from said front detector.

17. The method for performing dual-energy x-ray imaging of claim 16 wherein said two-dimensional projection mass densities A and B along said projection lines are calculated from said image pair $D_{fHph}$(x,y) and $D_{fLph}$(x,y).

18. The method for performing dual-energy x-ray imaging of claim 17 wherein said projection mass densities A and B are calculated by solving a nonlinear dual-energy equation system for said projection mass densities A and B using the dual-energy data decomposition method, wherein said equation system is $$D_{fHph}(x,y) = \int [\Phi_{0H}(E) \times \exp(-(\mu_A(E) \times A(x,y) + \mu_B(E) \times B(x,y)))] \times S_f(E) dE$$

and $$D_{fLph}(x,y) = \int [\Phi_{0L}(E) \times \exp(-(\mu_A(E) \times A(x,y) + \mu_B(E) \times B(x,y)))] \times S_f(E) dE.$$

19. The method for performing dual-energy x-ray imaging of claim 16 wherein said image pair $D_{fHpl}$(x(i),y(j)) and $D_{fLpl}$(x(i),y(j)) is calculated by the steps of:

(a) solving a nonlinear dual-energy equation system for said projection mass densities A and B through a numerical inversion method using an equation system $$D_{rHpl}(i,j) = \int [\Phi_{0H}(E) \times \exp(-(\mu_A(E) \times A(i,j) + \mu_B(E) \times B(i,j)))] \times S_r(E) dE$$

and $$D_{rLpl}(i,j) = \int [\Phi_{0L}(E) \times \exp(-(\mu_A(E) \times A(i,j) + \mu_B(E) \times B(i,j)))] \times S_r(E) dE;$$

(b) inserting said A and B solutions into equations for said image $$D_{fHpl}(x(i),y(j)) = \int [\Phi_{0H}(E) \times S_f(E)] \times \exp(-(\mu_A(E) \times A(i,j) + \mu_B(E) \times B(i,j))) dE$$

and $$D_{fLpl}(x(i),y(j)) = \int [\Phi_{0L}(E) \times S_f(E)] \times \exp(-(\mu_A(E) \times A(i,j) + \mu_B(E) \times B(i,j))) dE.$$

20. The method for performing dual-energy x-ray imaging of claim 16 wherein said image pair $D_{fHpl}$(x(i),y(j)) and $D_{fLpl}$(x(i),y(j)) is calculated from said image pair $D_{rHpl}$(i,j) and $D_{rLpl}$(i,j) by using direct quantitative relationships $$D_{fHpl}(x(i),y(j)) = D_{fHpl}(D_{rHpl}(i,j), D_{rLpl}(i,j)) \text{ and}$$

$$D_{fLpl}(x(i),y(j)) = D_{fLpl}(D_{rHpl}(i,j), D_{rLpl}(i,j)).$$

21. The method for performing dual-energy x-ray imaging of claim 16 wherein said image pair $D_{fHpl}$(x(i), (j)) and $D_{fLpl}$(x(i),y(j)) is calculated from said image pair $D_{rHpl}$(i,j) and $D_{rLpl}$(i,j) by solving a dual-energy primary x-ray imaging equation system through a linearization approximation method with corrections for beam hardening and higher-order effects.

22. A method for performing dual-energy x-ray imaging of a subject using an imaging system having two-dimensional x-ray detectors, said subject being composed substantially of two materials, $M_A$ and $M_B$, that interact differently with x-rays, said material $M_A$ having a two-dimensional projection mass density A and said material $M_B$ having a two-dimensional projection mass density B, said imaging system including, in physical sequence from front to back, an x-ray source, a front two-dimensional x-ray detector having a plurality of front detection locations identified by the notation (x,y), a beam selection means, and a rear two-dimensional x-ray detector assembly having a plurality of selected rear detection locations identified by the notation (i,j) and a plurality of shadowed rear detection locations identified by the notation (i',j'), said selected rear detection locations and said shadowed rear detection locations being mutually exclusive, said subject being between said x-ray source and said front detector, said x-ray source being adapted to emit x-rays for passage through said subject, said x-rays including primary x-rays having their direction of travel unaltered by interaction with said subject and said x-rays including scatter x-rays having their direction of travel altered by interaction with said subject, said front detector having selected detection locations, identified by the notation (x(i),y)j), that are intersected by x-ray projection lines extending from said x-ray source to said selected rear detection locations (i,j), said beam selection means permitting passage of said primary x-rays and said scatter x-rays to said selected rear detection locations, preventing passage of said primary x-rays to said shadowed rear detector locations, and allowing passage of said scatter x-rays to said shadowed rear detection locations, and said rear detector assembly including, in physical sequence from front to back, a low-energy detector, an x-ray energy spectral filter, and a high-energy detector, said method comprising the steps of:

(a) illuminating said subject with x-rays;

(b) acquiring a high-resolution image $I_{fh}$ from said front detection locations (x,y) and processing said image $I_{fh}$ to normalize it and to subtract dark signals, yielding an image $D_{fh}(x,y)$ which is composed of primary x-rays and scatter x-rays;

(c) producing, from said image $D_{fh}(x,y)$, a low-resolution image $D_{fl}(x(i),y(j))$ representing said selected front detection locations (x(i),y(j));

(d) acquiring a low-resolution image $I_{rHl}$, from said selected rear detection locations (i,j) of said high-energy detector and processing said image $I_{rHl}$ to normalize it and to subtract dark signals, yielding an image $D_{rHl}(i,j)$;

(e) acquiring a low-resolution image $I_{rLl}$ from said selected rear detection locations (i,j) of said low-energy detector and processing said image $I_{rLl}$ to normalize it and to subtract dark signals, yielding an image $D_{rLl}(i,j)$;

(f) acquiring a low-resolution scatter image $I_{rHsl}$ from said shadowed rear detection locations (i',j') of said high-energy detector and processing said image $I_{rHsl}$ to normalize it and to subtract dark signals, yielding an image $D_{rHsl}(i',j')$;

(g) acquiring a low-resolution scatter image $I_{rLsl}$ from said shadowed rear detection locations (i',j') of said low-energy detector and processing said image $I_{rLsl}$ to normalize it and to subtract dark signals, yielding an image $D_{rLsl}(i',j')$;

(h) calculating a low-resolution scatter image $D_{rHsl}(i,j)$ by extending said low-resolution scatter image $D_{rHsl}(i',j')$ to said selected rear detection locations (i,j) through interpolation and calculating a low-resolution scatter image $D_{rLsl}(i,j)$ by extending said low-resolution scatter image $D_{rLsl}(i',j')$ to said selected rear detection locations (i,j) through interpolation;

(i) calculating a low-resolution primary x-ray image pair $D_{rLpl}(i,j)$ and $D_{rHpl}(i,j)$ by subtracting said image $D_{rHsl}(i,j)$ from said image $D_{rHl}(i,j)$ to yield $D_{rHpl}(i,j)$ and subtracting said image $D_{rLsl}(i,j)$ from said image $D_{rLl}(i,j)$ to yield $D_{rLpl}(i,j)$;

(j) calculating a low-resolution primary x-ray image $D_{fpl}(x(i),y(j))$ from said low-resolution dual-energy primary x-ray image pair $D_{rHpl}(i,j)$ and $D_{rLpl}(i,j)$;

(k) calculating a low-resolution scatter x-ray image $D_{fsl}(x(i),y(j))$ by subtracting said image $D_{fpl}(x(i),y(j))$ from said image $D_{fl}(x(i),y(j))$;

(l) calculating a high-resolution scatter image $D_{fsh}(x,y)$ by extending said low-resolution scatter image $D_{fsl}(x(i),y(j))$ to the entire image area of said front detector through interpolation;

(j) calculating a high-resolution primary x-ray image $D_{fph}(x,y)$ at said front detector by subtracting said image $D_{fsh}(x,y)$ from said image $D_{fh}(x,y)$;

(k) whereby said image $D_{fph}(x,y)$ is a high-resolution, two-dimensional, primary x-ray image of said subject at said front detector after said scatter x-rays have been substantially eliminated, said image having a spatial resolution substantially equal to the highest spatial resolution available from said front detector.

23. The method for performing dual-energy x-ray imaging of claim 22 wherein said image $D_{fpl}(x(i),y(j))$ is calculated by the steps of:

(a) solving a nonlinear dual-energy equation system for said projection mass densities A and B through a dual-energy data decomposition method using an equation system $$D_{rHpl}(i,j) = \int [\Phi_{0H}(E) \times \exp(-(\mu_A(E) \times A(i,j) + \mu_B(E) \times B(i,j)))] \times S_r(E) dE$$

and $$D_{rLpl}(i,j) = \int [\Phi_{0L}(E) \times \exp(-(\mu_A(E) \times A(i,j) + \mu_B(E) \times B(i,j)))] \times S_r(E) dE;$$

and (b) inserting said A and B solutions into equations for said image $D_{fpl}(x(i),y(j)) = \int [\Phi_0(E) \times S_f(E)] \times \exp(-(\mu_A(E) \times A(i,j) + \mu_B(E) \times B(i,j))) dE$.

24. The method for performing dual-energy x-ray imaging of claim 22 wherein said image pair $D_{fHpl}(x(i),y(j))$ and $D_{fLpl}(x(i),y(j))$ is calculated from said image pair $(D_{rLpl}(i,j), D_{rHpl}(i,j))$ by using direct quantitative relationships $D_{fPl}((x(i),y(j))) = D_{fLpl}[D_{rLpl}(i,j)), D_{rHpl}(i,j)]$.

25. The method for performing dual-energy x-ray imaging of claim 22 wherein said image $D_{fpl}(x(i),y(j))$ is calculated from said image pair $D_{rHpl}(i,j)$ and $D_{rLpl}(i,j)$ by solving a dual-energy primary x-ray imaging equation system through using a linearization approximation method with corrections for beam hardening and higher order effects.

26. A method for performing data decomposition in dual-energy x-ray imaging of a subject using a two-dimensional imaging system, said imaging system including an x-ray source, a two-dimensional x-ray detector having a matrix of discrete detector cells identified by the notation (x,y), and detection means to determine a normalized, two-dimensional, dual-energy primary x-ray image pair of said subject at said detector cells, said subject being represented by two materials, $M_A$ and $M_B$, that interact differently with x-rays, said material $M_A$ having a two-dimensional projection mass density A(x,y) at said typical cell and said material $M_B$ having a two-dimensional projection mass density B(x,y), said A(x,y) and B(x,y) being defined along a projection line connecting said x-ray source and said detector cell (x,y), each of said detector cells (x,y) capable of being represented by a typical cell $(x_0,y_0)$ in terms of x-ray signals as a function of said projection mass densities, said data decomposition method comprising:

(a) applying said detection means to determine a two-dimensional primary x-ray image signal $D_H(x,y)$ at said detector cells at an average energy level H and a two-dimensional primary x-ray image signal $D_L(x,y)$ at said detector cells at an average energy level L different from said energy level H;

(b) constructing a first explicit quantitative function pair $$D_H(x_0,y_0) = F_{DH}(A(x_0,y_0), B(x_0,y_0)),$$

$$D_L(x_0,y_0) = F_{DL}(A(x_0,y_0), B(x_0,y_0))$$

for said typical detector cell $(x_0,y_0)$ in continuous domain of said projection mass densities A and B such that corresponding values of said $D_H$ and $D_L$ can be obtained for any pair of real number values of said A and B within a predetermined range, said first function pair having the shorthand notation $D_H = F_{DH}(A,B)$, $D_L = F_{DL}((A,B)$;

(c) numerically inverting said first function pair to obtain a second explicit quantitative function pair $$A(x_0,y_0) = F_A(D_H(x_0,y_0), D_L(x_0,y_0)),$$

$$B(x_0,y_0) = F_B(D_H(x_0,y_0), D_L(x_0,y_0))$$

in continuous domain such that corresponding values of said A and B can be obtained for any pair of real number values of said $D_H$ and $D_L$ within a predetermined range, said second function pair having the shorthand notation $A=F_A(D_H, D_L)$, $B=F_B(D_H, D_L)$; and (d) calculating material compositions $A(x,y)$ and $B(x,y)$ for said subject by substituting said primary x-ray image signal pair $D_H(x,y)$, $D_L(x,y)$ for said values $D_H(x_0,y_0)$, $D_L(x_0,Y_0)$ in said second function pair for all of said detector cells $(x,y)$;

(e) whereby said material compositions $A(x,y)$ and $B(x,y)$ of said subject represent a pair of two-dimensional projection mass density images along said projections lines at detector cell $(x,y)$.

27. The method of claim 26 wherein:

(a) said first function pair $D_H=F_{DH}(A,B)$, $D_L=F_{DL}(A,B)$ is constructed through providing energy-dependent functions of said imaging system $sps_H(E)$ and $sps_L(E)$ in explicit quantitative forms to the fundamental dual-energy x-ray equations as $$D_H(x_0,y_0)=\int sps_H(E)\times\exp(-(\mu_A(E)\times A(x_0,y_0)+\mu_B(E)\times B(x_0,y_0)))dE \text{ and}$$

$$D_L(x_0,y_0)=\int sps_L(E)\times\exp(-(\mu_A(E)\times A(x_0,y_0)+\mu_B(E)\times B(x_0,y_0)))dE;$$

(b) said function $sps_H(E)$ being separately determined by absorption method through using a reference material M of thickness t between said x-ray source and said x-ray detector, measuring a narrow-beam primary x-ray signal value $P_H(t)$ at said energy level H, and using a least-square parameter fitting method to obtain $sps_H(E)$ from the equation $$P_H(t)=\int sps_H(E)\times\exp(-(\mu_M(E)\times t)dE; \text{ and}$$

(c) said function $sps_L(E)$ being separately determined by absorption method through using said reference material M of thickness t between said x-ray source and said x-ray detector, measuring a narrow-beam primary x-ray signal value $P_L(t)$ at said energy level L, and using a least-square parameter fitting method to obtain $sps_L(E)$ from the equation $$P_L(t)=\int sps_L(E)\times\exp(-(\mu M (E)\times t)dE.$$

28. The method of claim 26 wherein said first function pair $D_H=F_{DH}(A,B)$, $D_L=F_{DL}((A,B)$ is obtained by directly measuring $D_H$ and $D_L$ values for said typical cell $(x_0,y_0)$ at a number of points with known values of A and B in a desired range of $(A,B)$ and analytically extending said $D_H$ and $D_L$ values to continuous domain.

29. The method of claim 26 wherein said numerical inversion from said first function pair $D_H=F_{DH}(A,B)$, $D_L=F_{DL}(A,B)$ to said second function pair $A=F_A(D_H, D_L)$, $B=F_B(D_H, D_L)$ being conducted by:

(a) calculating a first pair of arrays of values from the simultaneous equations $D_H=F_{DH}(A_n,B_m)$ and $D_L=F_{DL}(A_n,B_m)$ on an integer grid $(A_n,B_m)$, where $A_n=A_0,A_1,A_2,\ldots,A_N$ and $B_m=B_0,B_1,B_2,\ldots,B_m$ are integer indices of said first pair of arrays;

(b) numerically inverting said simultaneous equations $D_H=F_{DH}(A_n,B_m)$ and $D_L=F_{DL}(A_n,B_m)$ to obtain simultaneous equations $A^0=F_A{}^0(D_H[j],D_L[k])$ and $B^0=B_B{}^0(D_H[j],D_L[k])$;

(c) calculating a second pair of arrays of values from said simultaneous equations $A^0=F_A{}^0(D_H[j],D_L[k])$ and $B^0=F_B{}^0(D_H[j],D_L[k])$, where $D_H[j]=D_H[0],D_H[1],D_H[2],\ldots,D_H[J]$ and $D_L[k]=D_L[0],D_L[1],D_L[2],\ldots,D_L[K]$ are integers or real numbers and where $D_H[j]<D_H[j+1]$ and $D_L[k]<D_L[k+1]$, j, k, J, and K being integer indices of the coordinate arrays for said second pair of arrays;

(d) for each of said measured dual-energy signal data pair $D_H(x,y)$, $D_L(x,y)$, determining the closest indices j and k values according to the criteria $D_H[j]\leq D_H(x,y)\leq D_H[j+1]$ and $D_L[k]\leq D_L(x,y) \leq D_L[k+1]$, and then, from said closest indices j and k, determining said $A(x,y)$ and $B(x,y)$ from said simultaneous equations $A^0=F_A{}^0(D_H[j],D_L[k])$ and $B^0=F_B{}^0(D_H[j],D_L[k])$; and (e) refining said $A(x,y)$ and $B(x,y)$ to an accuracy as high as real numbers can provide from the equations $$A(x, y) = F_A^0(D_H[j], D_L[k]) +$$
$$[\partial F_A^0(D_H, D_L)/\partial D_H]_{D_H=D_H[j];D_L=D_L[k]} \times (D_H(x, y) - D_H[j]) +$$
$$[\partial F_A^0(D_H, D_L)/\partial D_L]_{D_H=D_H[j];D_L=D_L[k]} \times (D_L(x, y) - D_L[k]) +$$

higher order terms, and $$B(x, y) = F_B^0(D_H[j], D_L[k]) +$$
$$[\partial F_B^0(D_H, D_L)/\partial D_H]_{D_H=D_H[j];D_L=D_L[k]} \times (D_H(x, y) - D_H[j]) +$$
$$[\partial F_B^0(D_H, D_L)/\partial D_L]_{D_H=D_H[j];D_L=D_L[k]} \times (D_L(x, y) - D_L[k]) +$$

higher order terms.

* * * * *